(12) United States Patent
Wunberg et al.

(10) Patent No.: US 8,343,981 B2
(45) Date of Patent: Jan. 1, 2013

(54) HETEROCYCLYL-SUBSTITUTED DIHYDROQUINAZOLINES AND THEIR USE AS ANTIVIRAL AGENTS

(75) Inventors: Tobias Wunberg, Hinterbruehl (AT); Judith Baumeister, Mechelen (BE); Mario Jeske, Solingen (DE); Peter Nell, Woodside, CA (US); Susanne Nikolic, Monheim (DE); Frank Suessmeier, Wuppertal (DE); Holger Zimmermann, Wuppertal (DE); Rolf Grosser, Leverkusen (DE); Kerstin Henninger, Wuppertal (DE); Guy Hewlett, Haan (DE); Joerg Keldenich, Wuppertal (DE); Dieter Lang, Velbert (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 1713 days.

(21) Appl. No.: 10/556,198

(22) PCT Filed: Apr. 28, 2004

(86) PCT No.: PCT/EP2004/004456
§ 371 (c)(1),
(2), (4) Date: Feb. 9, 2007

(87) PCT Pub. No.: WO2004/099212
PCT Pub. Date: Nov. 18, 2004

(65) Prior Publication Data
US 2007/0185121 A1 Aug. 9, 2007

(30) Foreign Application Priority Data
May 9, 2003 (DE) .................................. 103 20 780

(51) Int. Cl.
*A01N 43/54* (2006.01)
*A61K 31/517* (2006.01)
(52) U.S. Cl. .................... 514/266.21; 544/284; 544/292
(58) Field of Classification Search .................. 514/250; 544/284
See application file for complete search history.

(56) References Cited

U.S. PATENT DOCUMENTS

| | | | |
|---|---|---|---|
| 5,854,245 A * | 12/1998 | Duggan et al. ................. | 514/250 |
| 7,196,086 B2 | 3/2007 | Wunberg et al. | |
| 7,271,260 B2 | 9/2007 | Lee et al. | |
| 2002/0019397 A1 | 2/2002 | Schnute et al. | |
| 2003/0216401 A1 * | 11/2003 | Bentley et al. ................. | 514/250 |
| 2005/0065160 A1 | 3/2005 | Wunberg et al. | |
| 2010/0179174 A1 | 7/2010 | Wunberg et al. | |
| 2010/0280021 A1 | 11/2010 | Berthel et al. | |

FOREIGN PATENT DOCUMENTS

| | | |
|---|---|---|
| EP | 1201765 | 5/2002 |
| WO | WO-99/41253 | 8/1999 |
| WO | WO-2004/041790 | 5/2004 |
| WO | WO-2004/072048 | 8/2004 |
| WO | WO-2004/096778 | 11/2004 |
| WO | WO-2004/099212 | 11/2004 |

OTHER PUBLICATIONS

Vippagunta et. al., "Crystalline solids", Advanced Drug Delivery Review, vol. 48 (2001), pp. 3-26.*
P.E. Pellett et al., The Family Herpesviridae: A Brief Introduction in, Fields' Virology 2479-2499, 2480 (David M. Knipe et al., eds., 5th ed., 2007).*
G. M Cleator et al., The Herpesviridae in, Principles and Practice of Clinical Virology 23-26, 23 (Arie J. Zuckerman et al., eds., 5th ed., 2004).*
P.D. Griffiths, Cytomegalovirus in, Principles and Practice of Clinical Virology 85-122 (A.J. Zuckerman et al., eds, 5th ed., 2001).*
T. Goldner, 85 Journal of Virology, 10884 (2011).*
Martinez et al., Antiviral Chem. Chemo. (2003) 14:107-114.
Wang et al., Tet. Letts. (1997) 38(50):8651-8654.
Desai et al., Indian J. Exp. Biol. (1998) 36(12):1280-1283 (abstract).
Desai et al., Farmaco (1996) 51(5):361-366 (abstract).
Griesser, Chapter 8, The Importance of Solvates (pp. 211-230), in the text, Polymorphism: In the Pharmaceutical Industry, Hilfiker, 2006.
Lee et al., Bioorg. Med. Chem. Lett. (2004) 14:3379-3384.
Lischka et al., Curr. Opin. Pharmacol. (Article in Press, Corrected Proof) (2008) 8:1-8.
Molina et al., Synthesis (1998) 3:283-287. Search Report from Ecuadorian Patent Application No. SP 05-6138, received Dec. 20, 2010, 1 page.
Viral Defense Found., http://www.viraldefense.org/mission.htm, downloaded Oct. 21, 2008.
Visiting Nurse Associations of America, http://www.vnaa.org/vnaa/gen/Germ_Protection_Center_Cold_and_Flu_Resources, downloaded Oct. 21, 2008.
Wikipedia, Maribavir, updated Feb. 10, 2009, http://en.wikipedia.org/wiki/Maribavir, downloaded Mar. 10, 2009.
Wilson et al., Med. Chem. Res. (1992) 2:102-110 (abstract).
Xin et al., Tetrahedron Lett. (2000) 41(8):1147-1150.

* cited by examiner

*Primary Examiner* — James O Wilson
*Assistant Examiner* — Alexander R Pagano
(74) *Attorney, Agent, or Firm* — Morrison & Foerster LLP

(57) ABSTRACT

The invention relates to heterocyclyl-substituted dihydroquinazolines of formula (I),

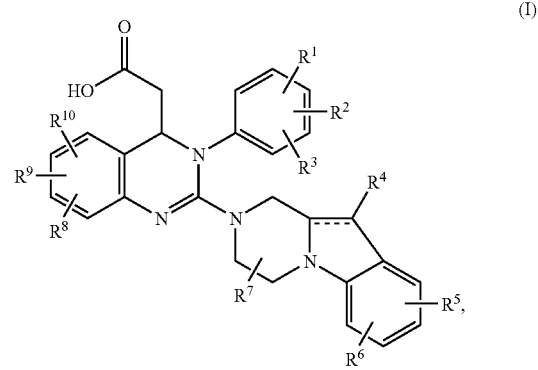

to processes for their preparation, to medicaments containing them, and to methods for the treatment and/or prophylaxis of diseases, in particular, for use as anti-viral agents, in particular, against cytomegaloviruses.

23 Claims, No Drawings

HETEROCYCLYL-SUBSTITUTED DIHYDROQUINAZOLINES AND THEIR USE AS ANTIVIRAL AGENTS

The invention relates to heterocyclyl-substituted dihydroquinazolines and to processes for their preparation, and also to their use for preparing medicaments for the treatment and/or prophylaxis of diseases, in particular for use as antiviral agents, in particular against cytomegaloviruses.

The synthesis of dihydroquinazolines is described in Saito T., et al. *Tetrahedron Lett.*, 1996, 37, 209-212 and in Wang F., et al. *Tetrahedron Lett.*, 1997, 38, 8651-8654.

Agents with antiviral activity and a different structure are available on the market; however, it is always possible for resistance to develop. Novel agents for an effective therapy are therefore desirable.

One object of the present invention is therefore to provide novel compounds having the same or improved antiviral action for the treatment of viral infective diseases in humans and animals.

It has been found, surprisingly, that the heterocyclyl-substituted dihydroquinazolines described in the present invention have antiviral action.

The present invention provides compounds of the formula

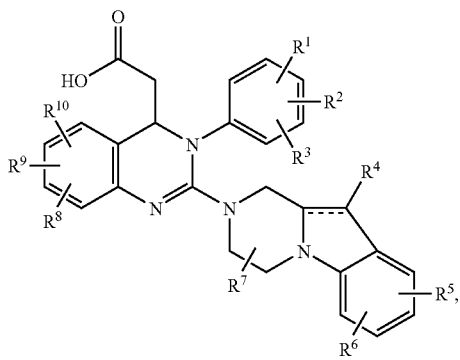

(I)

in which

╌╌╌╌ represents a single or double bond, $R^1$ represents hydrogen, amino, alkyl, alkoxy, alkylamino, alkylthio, cyano, halogen, nitro or trifluoromethyl, $R^2$ represents hydrogen, alkyl, alkoxy, alkylthio, cyano, halogen, nitro or trifluoromethyl, $R^3$ represents amino, alkyl, alkoxy, alkylamino, alkylthio, cyano, halogen, nitro, trifluoromethyl, alkylsulphonyl or alkylaminosulphonyl or one of the radicals $R^1$, $R^2$ and $R^3$ represents hydrogen, alkyl, alkoxy, cyano, halogen, nitro or trifluoromethyl and the other two together with the carbon atoms to which they are attached form a 1,3-dioxolane, a cyclopentane ring or a cyclohexane ring, $R^4$ represents hydrogen or alkyl, $R^5$ represents hydrogen, alkyl, alkoxy, formyl, carboxyl, alkylcarbonyl, alkoxycarbonyl, trifluoromethyl, halogen, cyano, hydroxyl, amino, alkylamino, aminocarbonyl or nitro,
  where alkyl may be substituted by 1 to 3 substituents, where the substituents are selected independently of one another from the group consisting of halogen, amino, alkylamino, hydroxyl and aryl, $R^6$ represents hydrogen, alkyl, alkoxy, formyl, carboxyl, alkylcarbonyl, alkoxycarbonyl, trifluoromethyl, halogen, cyano, hydroxyl, amino, alkylamino, aminocarbonyl or nitro,
  where alkyl may be substituted by 1 to 3 substituents, where the substituents are selected independently of one another from the group consisting of halogen, amino, alkylamino, hydroxyl and aryl or $R^5$ and $R^6$ together with the carbon atoms to which they are attached form a 1,3-dioxolane, a cyclopentane ring or a cyclohexane ring, $R^7$ represents hydrogen or alkyl, $R^8$ represents hydrogen, alkyl, alkoxy, alkylamino, alkylthio, formyl, carboxyl, aminocarbonyl, alkylaminocarbonyl, alkylcarbonyl, alkoxycarbonyl, trifluoromethyl, halogen, cyano, hydroxyl, nitro or a 5- to 7-membered heterocycle which is attached via nitrogen, $R^9$ represents hydrogen, alkyl, alkoxy, alkylthio, formyl, carboxyl, alkylcarbonyl, alkoxycarbonyl, trifluoromethyl, halogen, cyano, hydroxyl or nitro and $R^{10}$ represents hydrogen, alkyl, alkoxy, alkylthio, formyl, carboxyl, alkylcarbonyl, alkoxycarbonyl, trifluoromethyl, halogen, cyano, hydroxyl or nitro, and their salts, their solvates and the solvates of their salts.

Compounds according to the invention are the compounds of the formula (I) and their salts, solvates and solvates of the salts, compounds mentioned hereinbelow as embodiment(s) and their salts, solvates and solvates of the salts, if the compounds mentioned hereinbelow, embraced by formula (I), are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereo-isomerically pure constituents can be isolated in a known manner from such mixtures of enantiomers and/or diastereomers.

If the compounds according to the invention can exist in tautomeric forms, the present invention also provides all tautomeric forms.

Salts in the context of the present invention are physiologically acceptable salts of the compounds according to the invention. Also provided, however, are salts which for their part are not suitable for pharmaceutical applications but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the present invention, solvates are those forms of the compounds according to the invention which form a complex in the solid or liquid state by coordination with solvent molecules. Hydrates are a special form of solvates in which the coordination takes place with water.

For the purposes of the present invention, unless specified otherwise, the substituents have the following meanings:

Alkyl per se and "alk" and "alkyl" in alkoxy, alkylthio, alkylamino, alkylaminocarbonyl, alkylcarbonyl, alkylsulphonyl, alkylaminosulphonyl and alkoxycarbonyl are a straight-chain or branched alkyl radical having generally 1 to 6, preferably 1 to 4, particularly preferably 1 to 3, carbon atoms, by way of example and preferably methyl, ethyl, n-propyl, isopropyl, tert-butyl, n-pentyl and n-hexyl.

Alkoxy is, by way of example and preferably, methoxy, ethoxy, n-propoxy, isopropoxy, tert-butoxy, n-pentoxy and n-hexoxy.

Alkylthio is, by way of example and preferably, methylthio, ethylthio, n-propylthio, isopropylthio, tert-butylthio, n-pentylthio and n-hexylthio.

Alkylamino is an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino is, for example, a monoalkylaminocarbonyl radical having 1 to 3 carbon atoms or is a dialkylaminocarbonyl radical having 1 to 3 carbon atoms each per alkyl substituent.

Alkylaminocarbonyl is an alkylaminocarbonyl radical having one or two alkyl substituents (chosen independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl is, for example, a monoalkylaminocarbonyl radical having 1 to 3 carbon atoms or is a dialkylaminocarbonyl radical having 1 to 3 carbon atoms each per alkyl substituent.

Alkylsulphonyl is, by way of example and preferably, methylsulphonyl, ethylsulphonyl, n-propylsulphonyl, isopropylsulphonyl, tert-butylsulphonyl, n-pentylsulphonyl and n-hexylsulphonyl.

Alkylaminosulphonyl is an alkylaminosulphonyl radical having one or two alkyl substituents (chosen independently of one another), by way of example and preferably methylaminosulphonyl, ethylaminosulphonyl, n-propylaminosulphonyl, isopropylaminosulphonyl, tert-butylaminosulphonyl, n-pentylaminosulphonyl, n-hexylaminosulphonyl, N,N-dimethylaminosulphonyl, N,N-diethylaminosulphonyl, N-ethyl-N-methylaminosulphonyl, N-methyl-N-n-propylaminosulphonyl, N-isopropyl-N-n-propylaminosulphonyl, N-tert-butyl-N-methylaminosulphonyl, N-ethyl-N-n-pentylaminosulphonyl and N-n-hexyl-N-methylaminosulphonyl. $C_1$-$C_3$-Alkylaminosulphonyl is, for example, a monoalkylaminosulphonyl radical having 1 to 3 carbon atoms or is a dialkylaminosulphonyl radical having 1 to 3 carbon atoms each per alkyl substituent.

Alkylcarbonyl is, by way of example and preferably, acetyl and propanoyl.

Alkoxycarbonyl is, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Aryl is a mono- to tricyclic aromatic carbocyclic radical having generally 6 to 14 carbon atoms; by way of example and preferably phenyl, naphthyl and phenanthrenyl.

A 5- to 7-membered heterocycle which is attached via nitrogen is a monocyclic non-aromatic heterocycle which is attached via nitrogen and generally has 5 to 7, preferably 5 or 6, ring atoms and up to 2, preferably up to 1, additional heteroatom and/or hetero group from the group consisting of N, O, S, SO, $SO_2$. The heterocycle may be saturated or partially unsaturated. Preference is given to 5- or 6-membered monocyclic saturated heterocycles having up to one additional heteroatom from the group consisting of O, N and S, such as, by way of example and preferably, pyrrolidinyl, piperidinyl, piperazinyl, morpholinyl and thiomorpholinyl.

Halogen is fluorine, chlorine, bromine and iodine, preferably fluorine and chlorine.

A symbol * on a carbon atom means that the compound, with respect to the configuration at this carbon atom, is present in enantiomerically pure form which, for the purposes of the present invention, is to be understood as meaning an enantiomeric excess of more than 90% (>90% ee).

Preference is given to those compounds of the formula (I) in which

╌╌╌╌ represents a single or double bond, $R^1$ represents hydrogen, $C_1$-$C_6$-alkyl, $C_1$-$C_6$-alkoxy, $C_1$-$C_6$-alkylthio, fluorine or chlorine, $R^2$ represents hydrogen, $C_1$-$C_6$-alkyl, $C_1$-$C_6$-alkoxy, $C_1$-$C_6$-alkylthio, fluorine or chlorine, $R^3$ represents $C_1$-$C_4$-alkyl, cyano, fluorine, chlorine, nitro or trifluoromethyl, or one of the radicals $R^1$, $R^2$ and $R^3$ represents hydrogen, $C_1$-$C_3$-alkyl, $C_1$-$C_3$-alkoxy, cyano, halogen, nitro or trifluoromethyl and the other two together with the carbon atoms to which they are attached form a cyclopentane ring or a cyclohexane ring, $R^4$ represents hydrogen, $R^5$ represents hydrogen, $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino or nitro, $R^6$ represents hydrogen, $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino or nitro or $R^5$ and $R^6$ together with the carbon atoms to which they are attached form a 1,3-dioxolane, $R^7$ represents hydrogen or methyl, $R^8$ represents $C_1$-$C_3$-alkyl, $C_1$-$C_3$-alkoxy, carboxyl, aminocarbonyl, $C_1$-$C_3$-alkylaminocarbonyl, trifluoromethyl, fluorine, chlorine, cyano, hydroxyl or nitro, $R^9$ represents hydrogen, $C_1$-$C_3$-alkyl, $C_1$-$C_3$-alkoxy, fluorine, chlorine, cyano or hydroxyl and $R^{10}$ represents hydrogen, $C_1$-$C_3$-alkyl, $C_1$-$C_3$-alkoxy, fluorine, chlorine, cyano or hydroxyl.

Among these, particular preference is given to compounds of the formula (I) in which ╌╌╌╌ represents a single or double bond, $R^1$ represents hydrogen, methyl, methoxy, methylthio, fluorine or chlorine,
$R^2$ represents hydrogen,
$R^3$ represents methyl, cyano, fluorine, chlorine, nitro or trifluoromethyl,
$R^4$ represents hydrogen,
$R^5$ represents hydrogen, methyl, methoxy, fluorine or chlorine,
$R^6$ represents hydrogen, methyl, methoxy, fluorine or chlorine,
$R^7$ represents hydrogen,
$R^8$ represents aminocarbonyl, fluorine, chlorine, cyano or hydroxyl,
$R^9$ represents hydrogen
and
$R^{10}$ represents hydrogen.

Preference is also given to those compounds of the formula (I) in which ----- represents a single bond.

Preference is also given to those compounds of the formula (I) in which $R^1$ represents hydrogen, methyl, methoxy or fluorine.

Among these, particular preference is given to those compounds of the formula (I) in which $R^1$ represents methoxy.

Preference is also given to those compounds of the formula (I) in which $R^1$ is attached to the phenyl ring via the position ortho to the point of attachment of the phenyl ring. For the purposes of the present invention, the point of attachment of the phenyl ring substituted by radicals $R^1$, $R^2$ and $R^3$ is to be understood as meaning the carbon atom of the phenyl ring which, according to formula (I), is attached to one of the two nitrogen atoms of the dihydroquinazoline.

Particular preference is given to those compounds of the formula (I) in which $R^1$ represents methoxy and $R^1$ is attached to the phenyl ring via the position ortho to the point of attachment of the phenyl ring.

Preference is also given to those compounds of the formula (I) in which $R^2$ represents hydrogen.

Preference is also given to those compounds of the formula (I) in which $R^3$ represents trifluoromethyl, chlorine, methyl, isopropyl or tert-butyl.

Among these, particular preference is given to those compounds of the formula (I) in which $R^3$ represents trifluoromethyl, chlorine or methyl.

Preference is also given to those compounds of the formula (I) in which $R^1$ is attached to the phenyl ring via the position ortho to the point of attachment of the phenyl ring and $R^3$ is attached to the phenyl ring via the position meta to the point of attachment of the phenyl ring, which position is opposite to that of $R^1$.

Particular preference is given to those compounds of the formula (I) in which $R^1$ is attached to the phenyl ring via the position ortho to the point of attachment of the phenyl ring, $R^3$ represents trifluoromethyl, chlorine or methyl and $R^3$ is attached to the phenyl ring via the position meta to the point of attachment of the phenyl ring, which position is opposite to that of $R^1$.

Preference is also given to those compounds of the formula (I) in which $R^4$ represents hydrogen.

Preference is also given to those compounds of the formula (I) in which $R^5$ represents hydrogen, methyl, methoxy, fluorine or chlorine.

Preference is also given to those compounds of the formula (I) in which $R^6$ represents hydrogen, methyl, methoxy or fluorine.

Preference is also given to those compounds of the formula (I) in which $R^7$ represents hydrogen.

Preference is also given to those compounds of the formula (I) in which $R^8$ represents fluorine.

Particular preference is given to those compounds of the formula (I) in which $R^8$ represents fluorine and $R^8$ is attached to the aromatic system of the dihydroquinazoline as described in formula

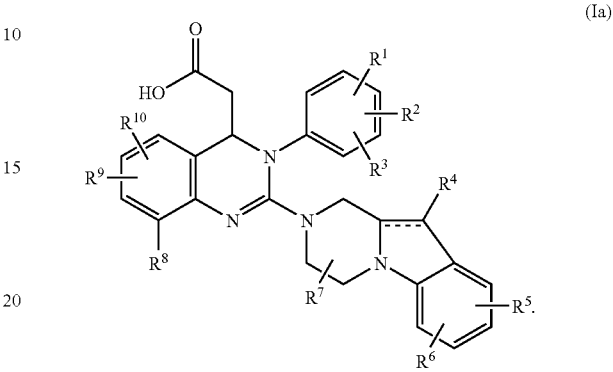

(Ia)

Preference is also given to those compounds of the formula (I) in which $R^9$ represents hydrogen.

Among these, particular preference is given to those compounds of the formula (I) in which $R^{10}$ represents hydrogen, methyl or fluorine.

The particular radical definitions given in the respective combinations or preferred combinations of radicals are, independently of the combinations of radicals given in each case, also replaced as desired by radical definitions of other combinations.

Very particular preference is given to combinations of one or more of the preferred ranges mentioned above.

The invention furthermore provides a process for preparing the compounds of the formula (I), which comprises,
according to process [A],
reacting compounds of the formula

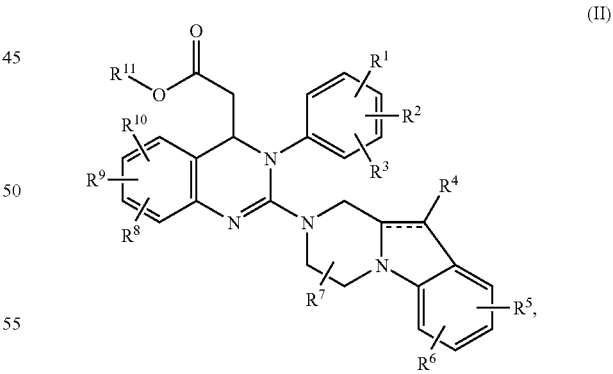

(II)

in which
----- $R^1$, $R^2$, $R^3$, $R^4$, $R^5$, $R^6$, $R^7$, $R^8$, $R^9$ and $R^{10}$ are as defined above,
and
$R^{11}$ represents alkyl, preferably methyl or ethyl,
with bases,
or,
according to process [B],
converting compounds of the formula

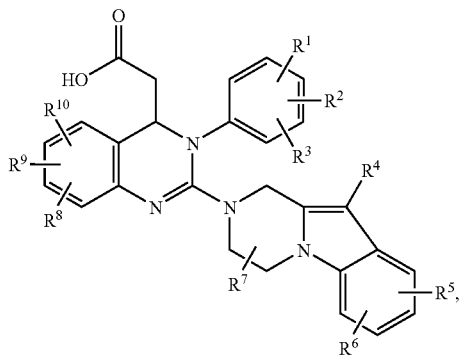

(Ib)

in which
$R^1$, $R^2$, $R^3$, $R^4$, $R^5$, $R^6$, $R^7$, $R^8$, $R^9$ and $R^{10}$ are as defined above,
by reaction with reducing agents into compounds of the formula

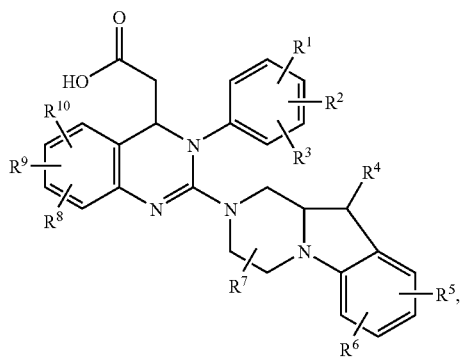

(Ic)

in which
$R^1$, $R^2$, $R^3$, $R^4$, $R^5$, $R^6$, $R^7$, $R^8$, $R^9$ and $R^{10}$ are as defined above.

The reaction according to process [A] is generally carried out in inert solvents, preferably in a temperature range of from room temperature to reflux temperature of the solvents, at atmospheric pressure.

Suitable bases are, for example, alkali metal hydroxides, such as sodium hydroxide, lithium hydroxide or potassium hydroxide, or alkali metal carbonates, such as caesium carbonate, sodium carbonate or potassium carbonate, if appropriate in aqueous solution; preference is given to sodium hydroxide in water.

Suitable inert solvents are, for example, ethers, such as 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, or mixtures of solvents; preference is given to dioxane or tetrahydrofuran.

The reaction according to process [B] is, if appropriate, carried out in inert solvents, preferably in a temperature range of from 0° C. to room temperature, at atmospheric pressure.

Suitable reducing agents are, for example, tin/hydrochloric acid, or hydrogenations with hydrogen using catalysts such as palladium-on-carbon, platinum, platinum oxide, Raney nickel, Rh(acac)(cod)-2PPh$_3$, and also combinations of hydride donors with acids.

Suitable hydride donors are, for example, sodium cyanoborohydride, potassium borohydride, BH$_3$-THF, [F$_3$CC(O)O]$_2$BH.THF or triethylsilane.

Suitable acids are, for example, carboxylic acids, such as acetic acid or trifluoroacetic acid.

Preference is given to sodium cyanoborohydride/glacial acetic acid, with acetic acid as solvent.

Suitable inert solvents are, for example, alcohols, such as methanol, ethanol or isopropanol, ethers, such as diethyl ether, tetrahydrofuran or dioxane; preference is given to ethanol.

The compounds of the formula (Ib) can be prepared according to process [A].

The compounds of the formula (II) are known or can be prepared by reacting compounds of the formula

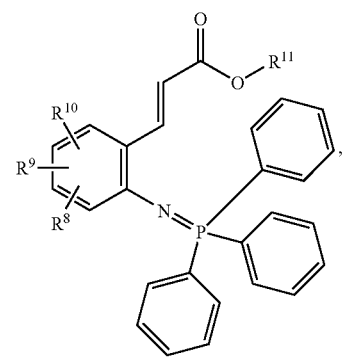

(III)

in which
$R^8$, $R^9$, $R^{10}$ and $R^{11}$ are as defined above
in a two-step reaction initially with compounds of the formula

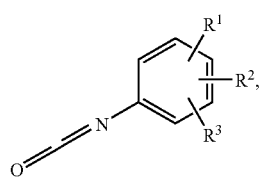

(IV)

in which
$R^1$, $R^2$ and $R^3$ are as defined above
and then with compounds of the formula

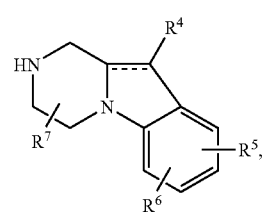

(V)

in which
$R^4$, $R^5$, $R^6$ and $R^7$ are as defined above.

Both steps of the reaction are generally carried out in inert solvents, preferably in a temperature range of from room temperature to 100° C., at atmospheric pressure. In the second step, if appropriate, silica gel is added to the reaction mixture. The reaction is preferably carried out with a work-up between the first and the second step.

Suitable inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylacetamide, acetonitrile or ethyl acetate, or mixtures of solvents; preference is given to methylene chloride.

The compounds of the formula (IV) are known or can be synthesized by known processes from the corresponding starting materials.

The compounds of the formula (V) are known or can be synthesized by known processes from the corresponding starting materials (for example J. Chang-Fong, et al., *Bioorg. Med. Chem. Lett.* 2002, 12, 155-158; Y. Nakamura, et al., *Org. Lett.* 2002, 4, 2317-2320; L. D. Basanagoudar, et al., *Ind. J. Chem.* 1991, 30B, 1014-1017; S. B. Rajur, et al., *Ind. J. Chem.* 1989, 28B, 1065-1068; A. C. Cheng, et al., *J. Org. Chem.,* 1982, 47, 5258-5262):

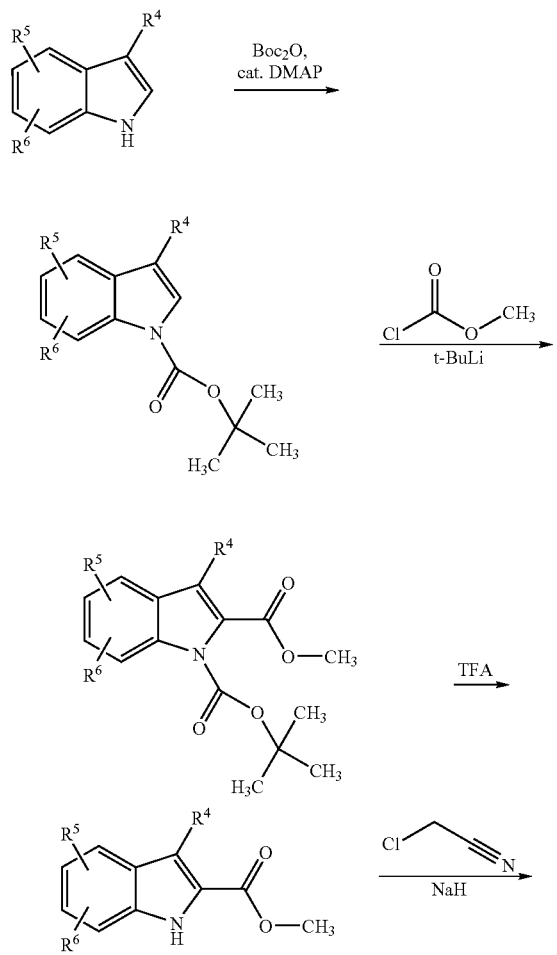

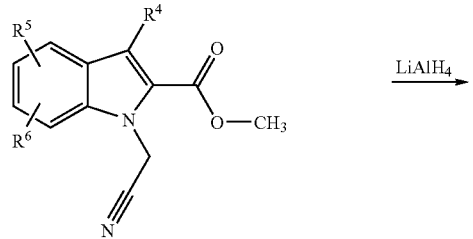

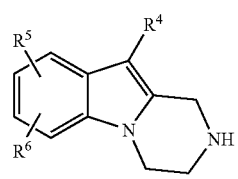

The starting materials required for this purpose are known or can be synthesized by known processes from the corresponding starting materials.

The compounds of the formula (III) are known or can be prepared by reacting compounds of the formula

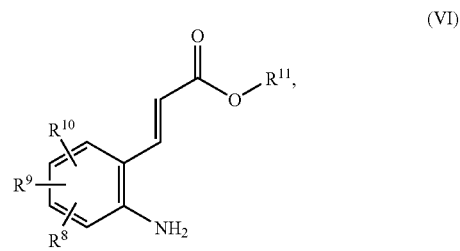

in which $R^8$, $R^9$, $R^{10}$ and $R^{11}$ are as defined above with triphenylphosphine and carbon tetrachloride.

The reaction is generally carried out in inert solvents, in the presence of a base, preferably in a temperature range of from room temperature to 50° C., at atmospheric pressure.

Suitable inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylacetamide, acetonitrile or pyridine; preference is given to acetonitrile.

Suitable bases are, for example, alkali metal and alkaline earth metal carbonates, such as caesium carbonate, sodium carbonate or potassium carbonate, or amines, such as triethylamine, diisopropylethylamine, N-methylmorpholine or pyridine; preference is given to triethylamine.

The compounds of the formula (VI) are known or can be synthesized by known processes from the corresponding starting materials, for example by a Heck reaction or a Wittig-Horner reaction according to the synthesis schemes below:

Heck Reaction:
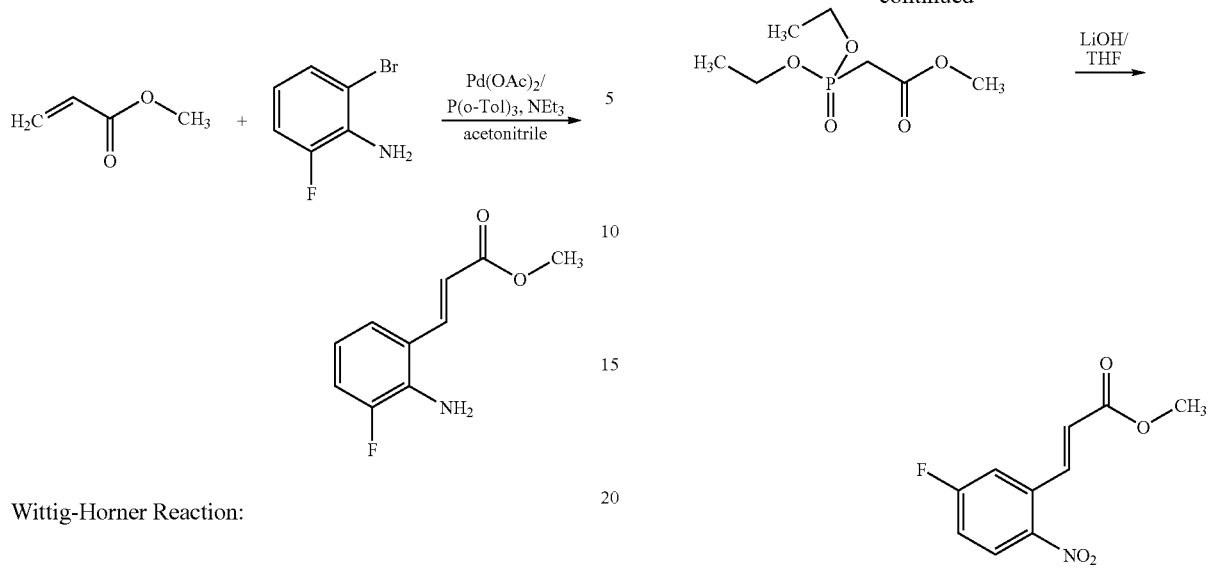
Wittig-Horner Reaction:
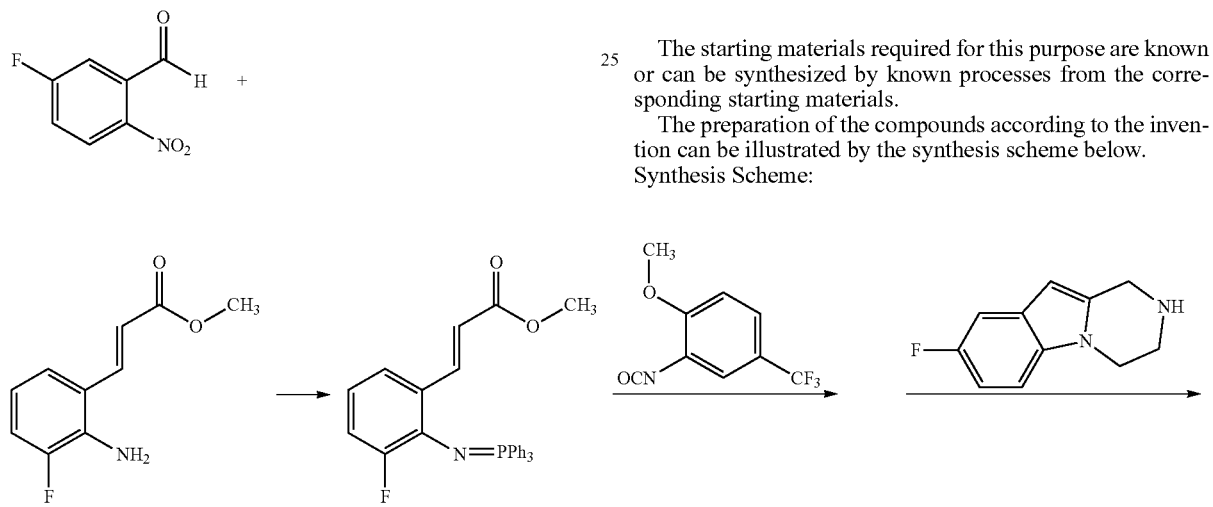
The starting materials required for this purpose are known or can be synthesized by known processes from the corresponding starting materials.
The preparation of the compounds according to the invention can be illustrated by the synthesis scheme below.
Synthesis Scheme:
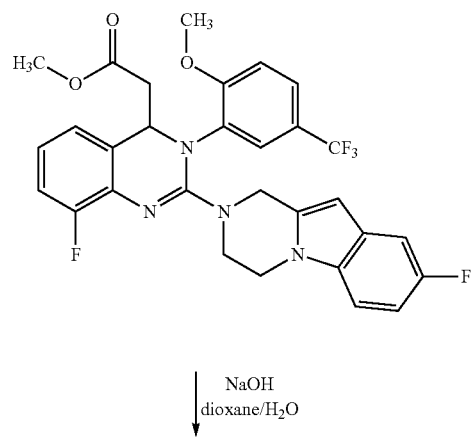

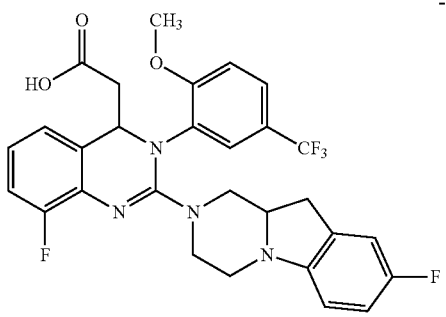 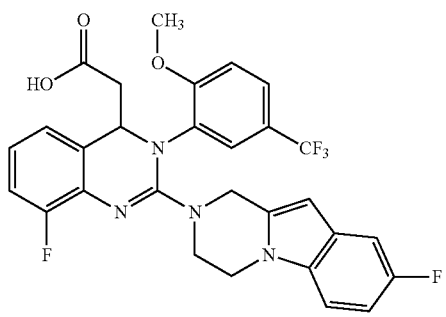

The compounds of the general formula (I) according to the invention show a surprising range of effects which could not have been predicted. They show an antiviral effect on representatives of the group of the Herpes viridae (Herpes viruses), especially on cytomegaloviruses (CMV), in particular on human cytomegalovirus (HCMV).

Areas of indication which may be mentioned by way of example are:
1) Treatment and prophylaxis of HCMV infections in AIDS patients (retinitis, pneumonitis, gastrointestinal infections).
2) Treatment and prophylaxis of cytomegalovirus infections in bone-marrow and organ transplantation patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.
6) Treatment of HCMV-positive cancer patients with the target to reduce HCMV-mediated tumour progression (cf. J. Cinatl et al., *FEMS Microbiology Reviews* 2004, 28, 59-77).

The present invention furthermore provides the use of the compounds according to the invention for the treatment and/or prophylaxis of diseases, especially viral infections, in particular with the viruses mentioned above, and the infective diseases caused thereby. Hereinbelow, a viral infection is to be understood as meaning both an infection with a virus and a disease caused by an infection with a virus.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The compounds according to the invention are preferably used for preparing medicaments suitable for the prophylaxis and/or treatment of infections with a representative of the group Herpes viridae, in particular a cytomegalovirus, in particular the human cytomegalovirus.

The present invention furthermore provides a method for the treatment and/or prophylaxis of disorders, in particular the disorders mentioned above, using an anti-virally effective amount of the compounds according to the invention.

The present invention furthermore provides medicaments comprising at least one compound according to the invention and at least one or more further active compounds, in particular for the treatment and/or prophylaxis of the disorders mentioned above. Active compounds which may be mentioned by way of example and by way of preference as being suitable for combinations are: antiviral active compounds, such as ganciclovir or acyclovir.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the compounds according to the invention in suitable administration forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitonealy). Administration forms suitable for parenteral administration are, inter alia, preparations for injection and infusion in the form of solutions, suspensions, emulsions, lyophilizates or sterile powders.

Examples suitable for other administration routes are, for example, pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems, milk, pastes, foams, dusting powders, implants or stents.

The active compounds according to the invention can be converted into the stated administration forms. This can take place in a manner known per se by mixing with inert nontoxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert non-toxic, pharmaceutically suitable auxiliaries, and their use for the purposes mentioned above.

In general, it has proved advantageous to administer on intravenous administration amounts of from about 0.001 to 10 mg/kg, preferably from about 0.01 to 5 mg/kg, of body weight to achieve effective results, and the dosage on oral administration is from about 0.01 to 50 mg/kg, preferably from 0.1 to 25 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

Abbreviations:
BINAP 2,2'-bis(diphenylphosphino)-1,1'-binaphthyl
Boc tert-butyloxycarbonyl
$CDCl_3$ deuterated chloroform
TLC thin-layer chromatography
DCI direct chemical ionization (in MS)
DCM dichloromethane
DIEA N,N-diisopropylethylamine
DMSO dimethyl sulphoxide
DMF N,N-dimethylformamide
EA ethyl acetate
EI electron impact ionization (in MS)
ESI electrospray ionization (in MS)
m.p. melting point
sat. saturated
h hour
HPLC high-pressure, high-performance liquid chromatography
conc. concentrated
LC-MS liquid chromatography-coupled mass spectroscopy
LDA lithium diisopropylamide
MTBE methyl tert-butyl ether
min minutes
MS mass spectroscopy
NMR nuclear magnetic resonance spectroscopy
Pd—C palladium-on-carbon
RP-HPLC reverse phase HPLC
RT room temperature
$R_t$ retention time (in HPLC)
THF tetrahydrofuran General LC-MS and HPLC Methods:

Method 1 (analytical HPLC): column: Kromasil C18 60 mm×2 mm; temperature: 30° C.; flow rate: 0.75 ml/min; mobile phase A: 0.005 M $HClO_4$, mobile phase B: acetonitrile; gradient: →0.5 min 98% A, →4.5 min 10% A, →6.5 min 10% A.

Method 2 (preparative HPLC): column: GromSil C18, 250 mm×30 mm; flow rate: 50 ml/min; run time: 38 min; mobile phase A: water, mobile phase B: acetonitrile; gradient: 10% B (3 min)→90% B (31 min)→90% B (34 min)→10% B (34.01 min); UV detection: 210 nm.

Method 3 (LC-MS): column: GromSil 120 (ODS-4 HE, 50 mm×2.0 mm, 3 µm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 4 (preparative HPLC, separation of enantiomers): column: chiral silica gel selector packing material KBD 8361 (250 mm×30 mm) based on the selector poly(N-methacryloyl-1-leucine-1-methylamide); temperature: 23° C.; mobile phase: methyl tert-butyl ether; flow rate: 100 ml/min; compound dissolved in MTBE/ethyl acetate (9:1).

Method 5 (LC-MS): column: GromSil 120 ODS-4 HE 50 mm×2 mm, 3.0 µm; mobile phase A: water+500 µl of 50% strength formic acid/l, mobile phase B: acetonitrile+500 µl of 50% strength formic acid/l, gradient: 0.0 min 0% B→2.9 min 70% B→3.1 min 90% B→4.5 min 90% B; oven: 50° C.; flow rate: 0.8 ml/min; UV detection: 210 nm.

Method 6 (LC-MS): Instrument: Micromass Quattro LCZ, HP1100; column: Symmetry C18, 50 mm×2.1 mm, 3.5 µm; mobile phase A: acetonitrile+0.1% formic acid, mobile phase B: water+0.1% formic acid; gradient: 0.0 min 10% A→4.0 min 90% A→6.0 min 90% A; oven: 40° C.; flow rate: 0.5 ml/min; UV detection: 208-400 nm.

Method 7 (LC-MS): column: GromSil 120 ODS-4 HE, 50 mm×2.0 mm, 3 µm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 8 (LC-MS): instrument type MS: Micromass ZQ; instrument type HPLC: Waters Alliance 2795; column: Merck Chromolith SpeedROD RP-18e 50 mm×4.6 mm; mobile phase A: water+500 µl of 50% strength formic acid/l; mobile phase B: acetonitrile+500 µl of 50% strength formic acid/l; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 9 (preparative HPLC, separation of enantiomers): column: Daicel silica gel phase Chiralpak AD; mobile phase: isohexane/ethanol/diethylamine (90/10/0.02; v/v/v).

Starting Materials

General Procedure [A]: Esterification of 2-nitrocinnamic acids with Methanol 517.7 mmol of 2-nitrocinnamic acid are initially charged in 600 ml of methanol, 20 drops of concentrated sulphuric acid are then added and the mixture is heated under reflux for 72 hours. After the reaction has ended (the reaction is monitored by TLC), the reaction solution is cooled in an ice bath. The crystals formed are filtered off with suction. The mother liquor is then concentrated slightly, and the crystals formed during this operation are filtered off with suction. Both fractions are combined and recrystallized from methanol at RT.

Example 1A

Methyl (2E)-3-(2-nitrophenyl)propenoate

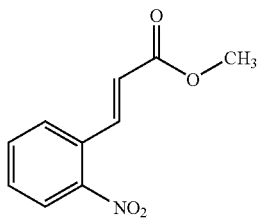

Starting with 100.0 g (517.7 mmol) of 2-nitrocinnamic acid, the general procedure [A] gives 72.6 g (68% of theory) of product.

HPLC (method 1): $R_t$=4.21 min

General Procedure [B]: Synthesis of Substituted 2-aminocinnamic acid Derivatives from 2-halo-substituted anilines by Heck Coupling In a one-necked flask, 1.0 equivalent of an aryl halide is initially charged in acetonitrile with 1.6 equivalents of methyl acrylate, 2.0 equivalents of triethylamine, 0.03 equivalents of palladium(II) acetate and 0.03 equivalents of tri-o-tolylphosphine (about 1M solution). The mixture is stirred under reflux for 48 hours. After the reaction has ended (the reaction is monitored by TLC), the solvent is removed. The residue is purified chromatographically on silica gel using cyclohexane/ethyl acetate=8:2 v/v.

Example 2A

Methyl (2E)-3-[2-amino-3-fluorophenyl]propenoate

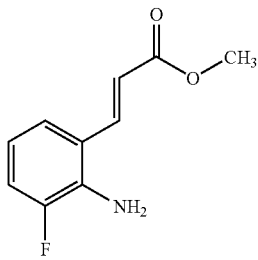

Starting with 42.00 g (221.04 mmol) of 2-bromo-6-fluoroaniline, the general procedure [B] gives 29.66 g (68% of theory) of product.

HPLC (method 1): $R_t$=4.14 min

MS (ESIpos): m/z=196 (M+H)$^+$

Example 3A

Methyl 2-amino-3-[(1E)-3-methoxy-3-oxo-1-propenyl]benzoate

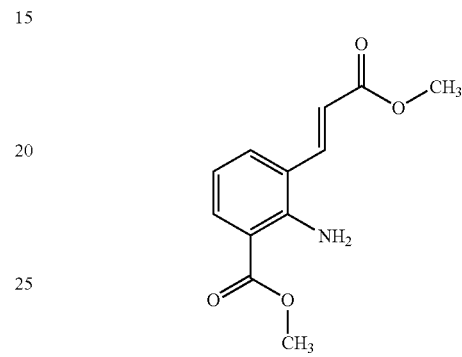

Starting with 2.00 g (8.69 mmol) of methyl 2-amino-3-bromobenzoate, the general procedure [B] gives 1.29 g (60% of theory) of product.

HPLC (method 1): $R_t$=4.42 min

MS (ESIpos): m/z=236 (M+H)$^+$

Example 4A

Methyl (2E)-3-[2-Amino-3,5-difluorophenyl]-2-propenoate

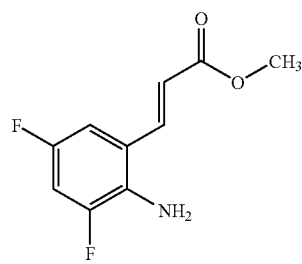

Starting with 3.00 g (14.42 mmol) of 2-bromo-4,6-difluoroaniline, the general procedure [B] gives 1.41 g (45% of theory) of product.

HPLC (method 1): $R_t$=4.23 min

MS (ESIpos): m/z=214 (M+H)$^+$

Example 5A

Methyl 4-amino-3-[(1E)-3-methoxy-3-oxo-1-propenyl]benzoate

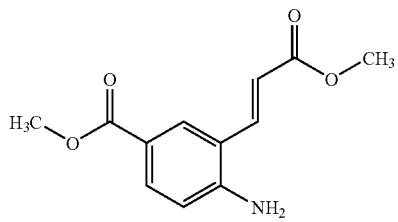

Starting with 25.00 g (90.23 mmol) of methyl 4-amino-3-iodobenzoate, the general procedure [B] gives 24.31 g (92% of theory) of product.

HPLC (method 1): $R_t$=4.71 min
MS (ESIpos): m/z=278 (M+H)$^+$

Example 6A

Methyl (2E)-3-[2-amino-5-cyanophenyl]-2-propenoate

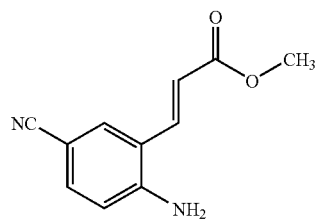

Starting with 1.90 g (9.64 mmol) of 3-bromo-4-aniinobenzonitrile, the general procedure [B] gives 1.28 g (50% of theory) of product.

HPLC (method 1): $R_t$=2.85 min
MS (DCIpos): m/z=220 (M+NH$_4$)$^+$

General Procedure [C]: Synthesis of Substituted 2-nitrocinnamic acid Derivatives from 2-halosubstituted benzaldehydes by Wittig-Horner Reaction In a 100 ml one-necked flask, 27.5 mmol of methyl diethylphosphonoacetate, 25.0 mmol of the benzaldehyde and 27.5 mmol of lithium hydroxide are suspended in tetrahydrofuran. After the reaction has ended (the reaction is monitored by TLC), an identical volume of water is added to the mixture. The aqueous phase is extracted three times with ethyl acetate. The combined organic phases are then washed with saturated sodium chloride solution and dried over sodium sulphate, and the solvent is removed. Without further purification, the product is dried under high vacuum at RT. In cases where many impurities are present, the product may be purified by column chromatography on silica gel using cyclohexane/ethyl acetate.

Example 7A

Methyl (2E)-3-(3-methoxy-2-nitrophenyl)-2-propenoate

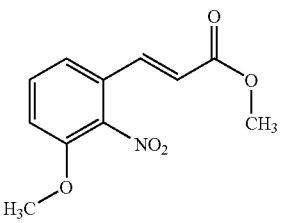 [SMILES: COC(=O)/C=C/c1cccc(OC)c1[N+](=O)[O-]]

Starting with 2.00 g (11.04 mmol) of 3-methoxy-2-nitrobenzaldehyde, the general procedure [C] gives 2.46 g (92% of theory) of product.

HPLC (method 1): $R_t$=4.37 min
MS (ESIpos): m/z=238 (M+H)$^+$

Example 8A

Methyl (2E)-3-(5-fluoro-2-nitrophenyl)-2-propenoate

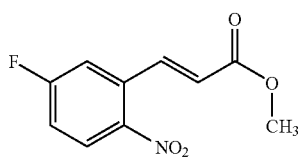

Starting with 20.0 g (118.3 mmol) of 5-fluoro-2-nitrobenzaldehyde, the general procedure [C] gives 7.25 g (27% of theory) of product.

MS (DCI): m/z=243 (M+NH$_4$)$^+$

General Procedure [D]: Preparation of a 2-nitrobenzaldehyde from a Benzyl Halide 10.0 mmol of the benzyl halide, 4.1 g of molecular sieve 4 Å and 20.0 mmol of N-methylmorpholine N-oxide are suspended in 45 ml of acetonitrile. Until complete conversion (the reaction is monitored by TLC), the mixture is stirred at RT. After the reaction has ended, the molecular sieve is filtered off, the solvent is evaporated and the residue is taken up again in ethyl acetate. This solution is washed initially with 1N hydrochloric acid and then with saturated sodium chloride solution. The organic phase is separated off and then dried over sodium sulphate, and the solvent is evaporated again.

According to an analytical examination, the crude product is sufficiently pure and can directly be reacted further.

Example 9A

2-Fluoro-6-nitrobenzaldehyde

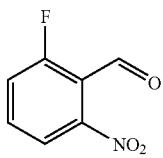

Starting with 2.00 g (8.55 mmol) of 3-fluoro-6-nitrobenzyl bromide, the general procedure [D] gives 1.09 g (75% of theory) of product.

HPLC (method 1): $R_t$=3.58 min

General Procedure [E]: Reduction of the Nitro Group of the 2-nitrocinnamic acid Derivatives Under argon, 25 mmol of the nitro compound and 125 mmol of tin(II) chloride dihydrate are initially charged in 60 ml of absolute ethanol in a 250 ml two-necked flask. This suspension is stirred under reflux for 30 minutes, and a clear solution is formed. The solution is then allowed to cool to room temperature and subsequently poured into ice-water. Using either solid sodium bicarbonate or a saturated sodium carbonate solution, the pH is adjusted to pH=7-8. 60 ml of ethyl acetate are then added, and the precipitated tin salts are filtered off through kieselguhr (a layer of a thickness of about 1 cm). The organic phase is separated off and the aqueous phase is re-extracted once with ethyl acetate. The organic phases are combined, washed once with saturated sodium chloride solution and dried over sodium sulphate, and the solvent is concentrated to about half of its original volume. Activated carbon corresponding to 1% of the weight of the nitro compound is then added, and the mixture is heated under reflux for 30 minutes (the colour of the solution changes). The activated carbon is filtered off and the solvent is removed. The residue is dried under high vacuum and, without further purification, used directly for the next step.

Example 10A

Methyl (2E)-3-[2-aminophenyl]propenoate

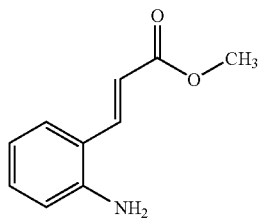

Starting with 15.00 g (72.34 mmol) of nitro compound, the general procedure [E] gives 12.05 g (94% of theory) of product.

LC-MS (method 6): $R_t$=3.29 min

Example 11A

Methyl 3-[2-amino-6-fluorophenyl]propenoate

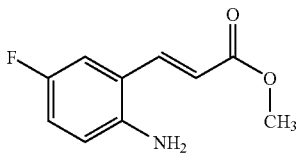

Starting with 7.25 g (32.2 mmol) of nitro compound from Example 8A, the general procedure [E] gives 5.0 g (58% of theory) of product.

HPLC (method 1): $R_t$=3.33 min

General Procedure [F]: Synthesis of the Iminophosphoranes by Appel Reaction of the Substituted Anilines In a 50 ml one-necked flask, 10.0 mmol of the 2-aminocinnamic ester, 20.0 mmol of triphenylphosphine, 100.0 mmol of carbon tetrachloride and 100.0 mmol of triethylamine are dissolved in 20 ml of acetonitrile. The mixture is stirred at room temperature for 2 hours. After the reaction has ended (the reaction is monitored by TLC or analytical HPLC), the solvent is removed under reduced pressure and the residue is purified by column chromatography on silica gel using cyclohexane/ethyl acetate=7:3.

Example 12A

Methyl (2E)-3-{3-fluoro-2-[(triphenylphosphoranylidene)amino]phenyl}propenoate

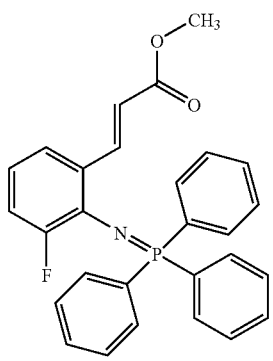 [SMILES: COC(=O)/C=C/c1cccc(F)c1N=P(c1ccccc1)(c1ccccc1)c1ccccc1]

Starting with 29.3 g (150.1 mmol) of amine compound from Example 2A, the general procedure [F] gives 55.0 g (80% of theory) of product.

HPLC (method 1): $R_t$=4.46 min

MS (ESIpos): m/z=456 (M+H)$^+$

Example 13A

Methyl (2E)-3-{5-fluoro-2-[(triphenylphosphoranylidene)amino]phenyl}propenoate

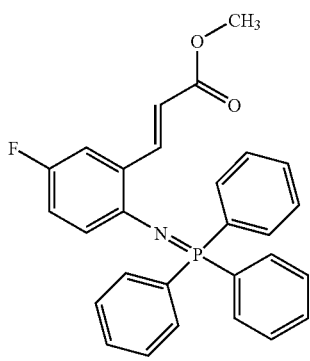 [SMILES: COC(=O)/C=C/c1cc(F)ccc1N=P(c1ccccc1)(c1ccccc1)c1ccccc1]

Starting with 50.0 g (256.2 mmol) of amine compound from Example 11A, the general procedure [F] gives 89.6 g (77% of theory) of product.

HPLC (method 1): $R_t$=4.36 min

MS (ESIpos): m/z=456 (M+H)$^+$

Example 14A

Methyl (2E)-3-{5-cyano-2-[(triphenylphosphoranylidene)amino]phenyl}propenoate

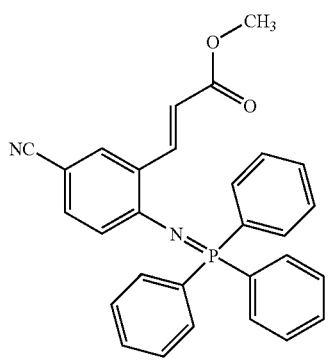

Starting with 1.24 g (4.60 mmol) of amine compound from Example 6A, the general procedure [F] gives 2.12 g (92% of theory) of product.

HPLC (method 1): $R_t$=4.42 min

MS (ESIpos): m/z=463 (M+H)$^+$

General Procedure [G]: Protection of Indoles Using tert-butyloxycarbonyl 7.6 mmol of indole and 9.2 mmol of di-tert-butyl carbonate are initially charged in 16 ml of acetonitrile, and 0.8 mmol of 4-dimethylaminopyridine are then added. The mixture is stirred at room temperature for 16 hours. After the reaction has ended (the reaction is monitored by TLC), 25 ml of ethyl acetate are added to the reaction solution. The organic phase is washed with 50 ml of water and 50 ml of a saturated aqueous sodium chloride solution and then dried over sodium sulphate and concentrated.

Example 15A tert-Butyl 4-methylindole-1-carboxylate

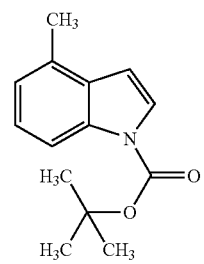 [SMILES: Cc1cccc2c1ccn2C(=O)OC(C)(C)C]

Starting with 1.0 g (7.6 mmol) of 4-methylindole, the general procedure [G] gives 1.8 g (98% of theory) of product.

HPLC (method 1): $R_t$=5.50 min

MS (ESIpos): m/z=232 (M+H)$^+$

Example 16A tert-Butyl 4-fluoroindole-1-carboxylate

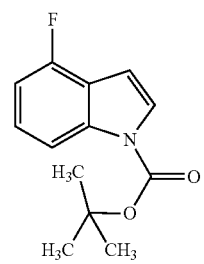 [SMILES: CC(C)(C)OC(=O)n1ccc2c(F)cccc21]

Starting with 3.0 g (22.2 mmol) of 4-fluoroindole, the general procedure [G] gives 5.1 g (97% of theory) of product.

HPLC (method 1): $R_t$=5.53 min

MS (ESIpos): m/z=236 (M+H)$^+$

Example 17A tert-Butyl 6-methylindole-1-carboxylate

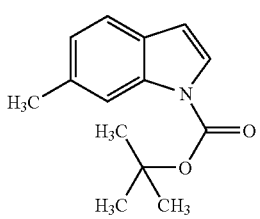 [SMILES: Cc1ccc2ccn(C(=O)OC(C)(C)C)c2c1]

Starting with 3.0 g (22.9 mmol) of 6-methylindole, the general procedure [G] gives 5.2 g (96% of theory) of product.

HPLC (method 1): $R_t$=5.68 min

MS (ESIpos): m/z=232 (M+H)$^+$

General Procedure [H]: Preparation of indole-2-carboxylic esters

Under argon, 7.8 mmol of tert-butyl indole-1-carboxylate are dissolved in 30 ml of absolute THF, and the mixture is cooled to −78° C. 11.7 mmol of tert-butyllithium (1.7M in pentane) are added slowly. The mixture is stirred at −78° C. for 60 minutes, 23.3 mmol of ethyl chloroformate are added slowly and the mixture is stirred at −78° C. for 10 minutes. Over a period of 30 minutes, the mixture is then warmed to room temperature, and the mixture is stirred at this temperature for a further 60 minutes. With ice-cooling, 10 ml of water are added, and the mixture is extracted with 25 ml of ethyl acetate. The aqueous phase is extracted with ethyl acetate (2×25 ml). The combined organic extracts are dried over sodium sulphate, concentrated and purified by column chromatography on silica gel (mobile phase cyclohexane/ethyl acetate=25:1).

Example 18A 1-tert-Butyl 2-ethyl 4-methylindole-1,2-dicarboxylate

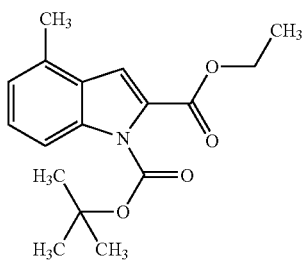 [SMILES: CCOC(=O)c1cc2c(C)cccc2n1C(=O)OC(C)(C)C]

Starting with 1.8 g (7.8 mmol) of Boc-protected 4-methylindole (Example 15A), the general procedure [H] gives 1.5 g (62% of theory) of product.

HPLC (method 1): $R_t$=5.30 min
MS (ESIpos): m/z=304 (M+H)$^+$

Example 19A 1-tert-Butyl 2-ethyl 4-fluoroindole-1,2-dicarboxylate

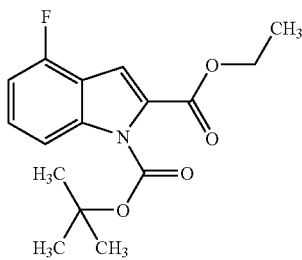 [SMILES: CCOC(=O)c1cc2c(F)cccc2n1C(=O)OC(C)(C)C]

Starting with 1.8 g (7.8 mmol) of Boc-protected 4-fluoroindole (Example 16A), the general procedure [H] gives 1.5 g (62% of theory) of product.

HPLC (method 1): $R_t$=5.30 min
MS (ESIpos): m/z=308 (M+H)$^+$

Example 20A 1-tert-Butyl 2-ethyl 6-methylindole-1,2-dicarboxylate

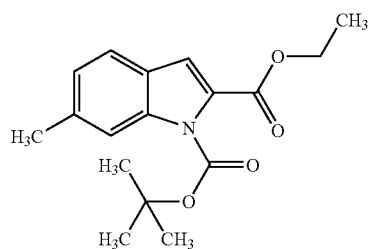 [SMILES: CCOC(=O)c1cc2ccc(C)cc2n1C(=O)OC(C)(C)C]

Starting with 1.5 g (6.5 mmol) of Boc-protected 6-methylindole (Example 17A), the general procedure [H] gives 1.0 g (48% of theory) of product.

HPLC (method 1): $R_t$=5.60 min
MS (ESIpos): m/z=290 (M+H)$^+$

General Procedure [J]: Removal of the Boc Protective Group

In a 25 ml one-necked flask, 4.8 mmol of the Boc-protected indole derivative are initially charged, and a dichloromethane/trifluoroacetic acid mixture (4:1) which corresponds to 9.7 mmol of trifluoroacetic acid is added. The reaction mixture is stirred at room temperature for 2 hours. After the reaction has ended (the reaction is monitored by TLC), the solvent is removed under reduced pressure and the product is dried under reduced pressure.

Example 21A

Ethyl 4-methylindole-2-carboxylate

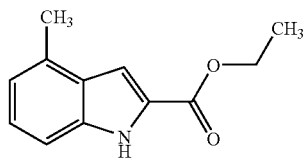

Starting with 1.5 g (4.8 mmol) of Boc-protected indole derivative from Example 18A, the general procedure [J] gives 0.9 g (94% of theory) of product.

HPLC (method 1): $R_t$=4.70 min
MS (ESIpos): m/z=204 (M+H)$^+$

Example 22A

Ethyl 4-fluoroindole-2-carboxylate

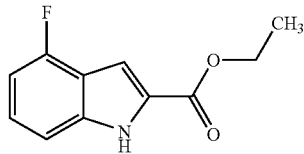

Starting with 1.0 g (3.3 mmol) of Boc-protected indole derivative from Example 19A, the general procedure [J] gives 0.6 g (88% of theory) of product.
HPLC (method 1): $R_t$=4.69 min
MS (ESIpos): m/z=208 (M+H)$^+$ Example 23A Ethyl 6-methylindole-2-carboxylate

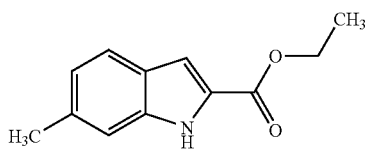

Starting with 1.3 g (4.3 mmol) of Boc-protected indole derivative from Example 20A, the general procedure [J] gives 0.8 g (96% of theory) of product.
LC-MS (method 8): $R_t$=2.33 min
MS (ESIpos): m/z=157 (M—OCH$_2$CH$_3$+H)$^+$ General Procedure [K]: Synthesis of the 1-cyanomethylindole Under argon, 4.6 mmol of indole-2-carboxylic ester are dissolved in 10 ml of N,N-dimethylformamide, and 5.5 mmol of sodium hydride (60% in mineral oil) are added a little at a time. After the addition, the mixture is stirred until the evolution of gas has ceased (about 30 minutes). The mixture is then cooled to 0° C., and 5.5 mmol of chloroacetonitrile are added. The mixture is stirred at room temperature for 16 hours. Ethyl acetate is added to the mixture, and the mixture is washed with water and a saturated aqueous sodium chloride solution. The organic phase is dried over sodium sulphate and concentrated.

Example 24A

Ethyl 1-cyanomethyl-4-methyl-1H-indole-2-carboxylate

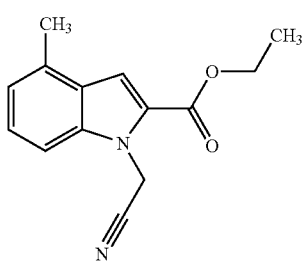 [SMILES: CCOC(=O)c1cc2c(C)cccc2n1CC#N]

Starting with 0.9 g (4.6 mmol) of ethyl 4-methylindole-2-carboxylate (Example 21A), the general procedure [K] gives 1.0 g (90% of theory) of product.
HPLC (method 1): $R_t$=4.86 min
MS (ESIpos): m/z=243 (M+H)$^+$ Example 25A Ethyl 1-cyanomethyl-4-fluoro-1H-indole-2-carboxylate

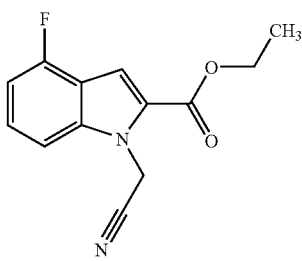 [SMILES: CCOC(=O)c1cc2c(F)cccc2n1CC#N]

Starting with 610 mg (2.9 mmol) of ethyl 4-fluoroindole-2-carboxylate (Example 22A), the general procedure [K] gives 644 mg (89% of theory) of product.
HPLC (method 1): $R_t$=4.86 min
MS (ESIpos): m/z=247 (M+H)$^+$ Example 26A Ethyl 1-cyanomethyl-6-methyl-1H-indole-2-carboxylate

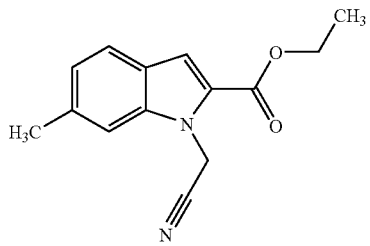 [SMILES: CCOC(=O)c1cc2ccc(C)cc2n1CC#N]

Starting with 871 mg (4.3 mmol) of ethyl 6-methylindole-2-carboxylate (Example 23A), the general procedure [K] gives 1080 mg (88% of theory) of product.
LC-MS (method 8): $R_t$=2.44 min
MS (ESIpos): m/z=243 (M+H)$^+$ Example 27A Methyl 1-cyanomethyl-4-methoxy-1H-indole-2-carboxylate

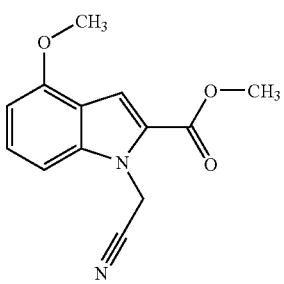 [SMILES: COC(=O)c1cc2c(OC)cccc2n1CC#N]

Starting with 5.0 g (24.4 mmol) of methyl 4-methoxyindole-2-carboxylate, the general procedure [K] gives 5.6 g (92% of theory) of product.
HPLC (method 1): $R_t$=4.34 min
MS (ESIpos): m/z=245 (M+H)$^+$

Example 28A

Methyl 1-cyanomethyl-6-methoxy-1H-indole-2-carboxylate

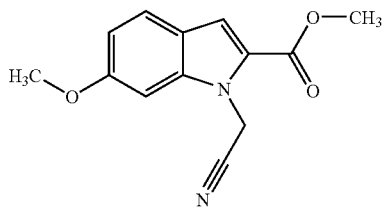

Starting with 500 mg (2.4 mmol) of methyl 6-methoxyindole-2-carboxylate, the general procedure [K] gives 460 mg (75% of theory) of product.
HPLC (method 1): $R_t$=4.42 min
MS (ESIpos): m/z=245 (M+H)$^+$

Example 29A

Ethyl 1-cyanomethyl-5-fluoro-1H-indole-2-carboxylate

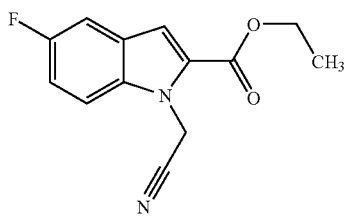 [SMILES: CCOC(=O)c1cc2cc(F)ccc2n1CC#N]

Starting with 5.2 g (24.9 mmol) of ethyl 5-fluoroindole-2-carboxylate, the general procedure [K] gives 5.5 g (88% of theory) of product.
HPLC (method 1): $R_t$=4.62 min
MS (ESIpos): m/z=247 (M+H)$^+$

Example 30A

Methyl 1-cyanomethyl-5-methyl-1H-indole-2-carboxylate

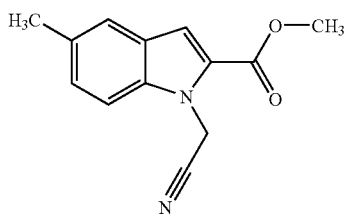

Starting with 250 mg (1.3 mmol) of methyl 5-methylindole-2-carboxylate, the general procedure [K] gives 200 mg (66% of theory) of product.
HPLC (method 1): $R_t$=4.61 min
MS (ESIpos): m/z=229 (M+H)$^+$ General Procedure [L]: Reduction of the Cyanomethylindoles to pyrazino[1,2-a]-indoles Under argon, a suspension of 22.4 mmol of 1-cyanomethylindole-2-carboxylic ester in 170 ml of diethyl ether is added slowly to a suspension of 53.7 mmol of lithium aluminium hydride in 100 ml of diethyl ether, and the mixture is then stirred under reflux for four hours. After the reaction has ended (the reaction is monitored by HPLC), 30 ml of a saturated aqueous ammonium chloride solution are carefully added to the mixture. Two batches of in each case 200 ml of ethyl acetate are added, and the mixture is stirred at 80° C. for ten minutes. The reaction mixture is filtered, the organic phase is washed with a saturated aqueous ammonium chloride solution (one batch of 200 ml), dried over sodium sulphate and concentrated, and the product is purified by column chromatography on silica gel (dichloromethane/methanol=50:1).

Example 31A

9-Methyl-1,2,3,4-tetrahydropyrazino[1,2-a]indole

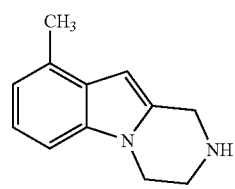

Starting with 1.1 g (4.3 mmol) of ethyl 1-cyano-4-methylindole-2-carboxylate (Example 24A), the general procedure [L] gives 235 mg (29% of theory) of product.
HPLC (method 1): $R_t$=3.68 min
MS (ESIpos): m/z=187 (M+H)$^+$

Example 32A

9-Fluoro-1,2,3,4-tetrahydropyrazino[1,2-a]indole

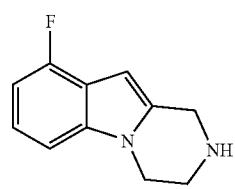 [SMILES: Fc1cccc2c1cc1n2CCNC1]

Starting with 632 mg (2.6 mmol) of ethyl 1-cyano-4-fluoroindole-2-carboxylate (Example 25A), the general procedure [L] gives 90 mg (18% of theory) of product.
LC-MS (method 5): $R_t$=1.67 min
MS (ESIpos): m/z=191 (M+H)$^+$

Example 33A

7-Methyl-1,2,3,4-tetrahydropyrazino[1,2-a]indole

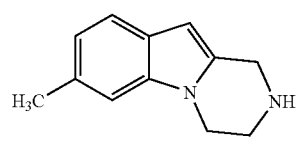

Starting with 1.08 g (3.8 mmol) of methyl 1-cyano-6-methylindole-2-carboxylate (Example 26A), the general procedure [L] gives 430 mg (61% of theory) of product.

LC-MS (method 3): $R_t$=1.62 min
MS (ESIpos): m/z=187 (M+H)$^+$

Example 34A

9-Methoxy-1,2,3,4-tetrahydropyrazino[1,2-a]indole

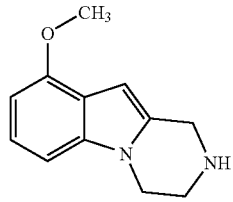

Starting with 433 mg (1.7 mmol) of methyl 1-cyano-4-methoxyindole-2-carboxylate (Example 27A), the general procedure [L] gives 143 mg (41% of theory) of product.

HPLC (method 1): $R_t$=3.46 min
MS (ESIpos): m/z=203 (M+H)$^+$

Example 35A

7-Methoxy-1,2,3,4-tetrahydropyrazino[1,2-a]indole

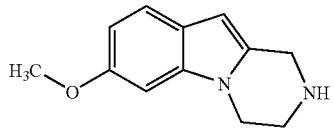

Starting with 430 mg (1.8 mmol) of methyl 1-cyano-6-methoxyindole-2-carboxylate (Example 28A), the general procedure [L] gives 172 mg (24% of theory) of product.

HPLC (method 1): $R_t$=3.49 min
MS (ESIpos): m/z=203 (M+H)$^+$

Example 36A

8-Fluoro-1,2,3,4-tetrahydropyrazino[1,2-a]indole

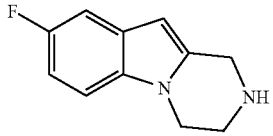 [SMILES: Fc1ccc2c(c1)cc1n2CCNC1]

Starting with 5.5 g (22.4 mmol) of ethyl 1-cyano-5-fluoroindole-2-carboxylate (Example 29A), the general procedure [L] gives 1.8 g (43% of theory) of product.

HPLC (method 1): $R_t$=3.52 min
MS (ESIpos): m/z=191 (M+H)$^+$

Example 37A

8-Methyl-1,2,3,4-tetrahydropyrazino[1,2-a]indole

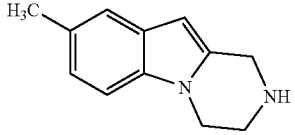

Starting with 170 mg (0.7 mmol) of methyl 1-cyano-5-methylindole-2-carboxylate (Example 30A), the general procedure [L] gives 88 mg (59% of theory) of product.

LC-MS (method 7): $R_t$=2.38 min
MS (ESIpos): m/z=187 (M+H)$^+$

General Procedure [M]: Reaction of an Iminophosphorane with an Isocyanate and Subsequent Reaction with an Amine to Give the Dihydroquinazoline Derivative 1.0 equivalent of the iminophosphorane is dissolved in 20 ml of dichloromethane (0.1-0.2M solution). 1.05 equivalents of a substituted isocyanate are then added, and the mixture is stirred at RT until the reaction has ended. The reaction is monitored by TLC or by analytical HPLC.

1.0 equivalent of amine and a spatula tip of silica gel are then added to the resulting solution of the carbodiimide in dichloromethane, and the mixture is stirred at room temperature until the reaction has gone to completion. After the reaction has ended (reaction is monitored by TLC or HPLC), the mixture is concentrated and purified by preparative HPLC on an RP phase.

In certain cases, the NMR shows the presence of a varying proportion of non-cyclized reaction product. In these cases, the mixture of cyclized and non-cyclized product is taken up in dioxane, a spatula tip of silica gel is added and the mixture is stirred under reflux for 30 min to 16 h. The silica gel is filtered off and the solution is used for further reactions.

Example 38A

Methyl [8-fluoro-3-(2-methoxy-5-trifluoromethylphenyl)-2-(9-methyl-3,4-dihydro-1H-pyrazino[1,2-a]indol-2-yl)-3,4-dihydroquinazolin-4-yl]acetate

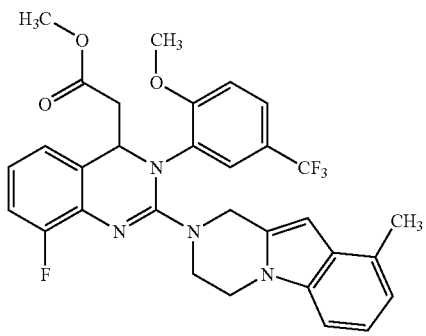 [SMILES: COC(=O)CC1c2cccc(F)c2N=C(N2CCn3c(cc4c(C)cccc43)C2)N1c1cc(C(F)(F)F)ccc1OC]

Starting with 563 mg (1.2 mmol) of the iminophosphorane from Example 12A, 268 mg (1.2 mmol) of 2-isocyanato-1-methoxy-4-(trifluoromethyl)benzene and 230 mg (1.2 mmol)

of 9-methyl-1,2,3,4-tetrahydropyrazino[1,2-a]indole from Example 31A, the general procedure [M] gives 325 mg (42% of theory) of product.

HPLC (method 1): $R_t$=4.98 min
MS (ESIpos): m/z=581 (M+H)$^+$

Example 39A

Methyl [8-fluoro-3-(2-methoxy-5-trifluorophenyl)-2-(9-fluoro-3,4-dihydro-1H-pyrazino[1,2-a]indol-2-yl)-3,4-dihydroquinazolin-4-yl]acetate

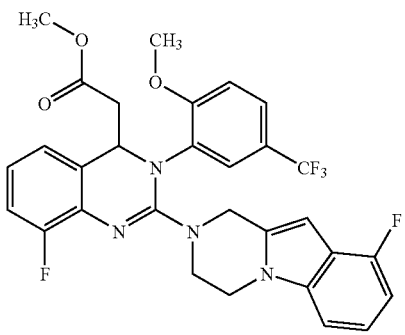 [SMILES: COC(=O)CC1c2cccc(F)c2N=C(N2CCn3c(cc4c(F)cccc43)C2)N1c1cc(C(F)(F)F)ccc1OC]

Starting with 192 mg (0.4 mmol) of the iminophosphorane from Example 12A, 91 mg (0.4 mmol) of 2-isocyanato-1-methoxy-4-(trifluoromethyl)benzene and 80 mg (0.4 mmol) of 9-fluoro-1,2,3,4-tetrahydropyrazino[1,2-a]indole from Example 32A, the general procedure [M] gives 78 mg (30% of theory) of product.

HPLC (method 1): $R_t$=4.98 min
MS (ESIpos): m/z=585 (M+H)$^+$

Example 40A

Methyl [8-fluoro-3-(2-methoxy-5-trifluoromethylphenyl)-2-(7-methyl-3,4-dihydro-1H-pyrazino[1,2-a]indol-2-yl)-3,4-dihydroquinazolin-4-yl)acetate

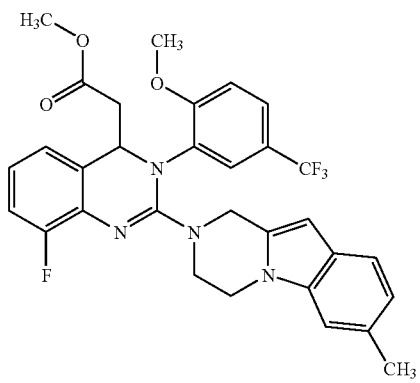 [SMILES: COC(=O)CC1c2cccc(F)c2N=C(N2CCn3c(cc4ccc(C)cc43)C2)N1c1cc(C(F)(F)F)ccc1OC]

Starting with 244 mg (0.5 mmol) of the iminophosphorane from Example 12A, 105 mg of 2-isocyanato-1-methoxy-4-(trifluoromethyl)benzene and 100 mg (0.5 mmol) of 9-methyl-1,2,3,4-tetrahydropyrazino[1,2-a]indole from Example 33A, the general procedure [M] gives 1 mg (1% of theory) of product.

LC-MS (method 3): $R_t$=3.51 min
MS (ESIpos): m/z=551 (M+H)$^+$

Example 41A

Methyl [8-fluoro-3-(2-methoxy-5-trifluoromethylphenyl)-2-(9-methoxy-3,4-dihydro-1H-pyrazino[1,2-a]indol-2-yl)-3,4-dihydroquinazolin-4-yl]acetate

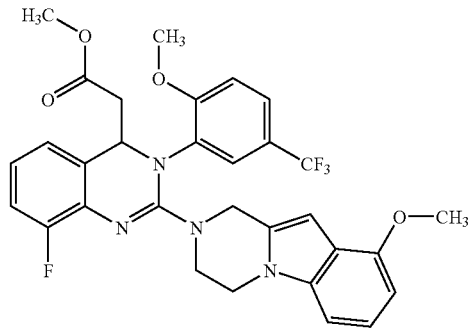 [SMILES: COC(=O)CC1c2cccc(F)c2N=C(N2CCn3c(cc4c(OC)cccc43)C2)N1c1cc(C(F)(F)F)ccc1OC]

Starting with 500 mg (1.1 mmol) of the iminophosphorane from Example 12A, 238 mg (1.1 mmol) of 2-isocyanato-1-methoxy-4-(trifluoromethyl)benzene and 222 mg (1.1 mmol) of 9-methoxy-1,2,3,4-tetrahydropyrazino[1,2-a]indole from Example 34A, the general procedure [M] gives 270 mg (38% of theory) of product.

HPLC (method 1): $R_t$=4.73 min
MS (ESIpos): m/z=597 (M+H)$^+$

Example 42A

Methyl {8-fluoro-2-(9-methoxy-3,4-dihydropyrazino[1,2-a]indol-2-yl)-3-[3-(trifluoromethyl)phenyl]-3,4-dihydroquinazolin-4-yl}acetate

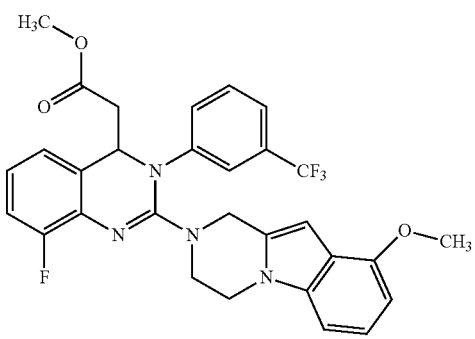 [SMILES: COC(=O)CC1c2cccc(F)c2N=C(N2CCn3c(cc4c(OC)cccc43)C2)N1c1cccc(C(F)(F)F)c1]

Starting with 281 mg (0.6 mmol) of the iminophosphorane from Example 12A, 134 mg (0.6 mmol) of 1-isocyanato-3-(trifluoromethyl)benzene and 129 mg (0.6 mmol) of 9-methoxy-1,2,3,4-tetrahydropyrazino[1,2-a]indole from Example 34A, the general procedure [M] gives 239 mg (66% of theory) of product.

HPLC (method 1): $R_t$=4.76 min
MS (ESIpos): m/z=567 (M+H)$^+$

Example 43A

Methyl {8-fluoro-2-(7-methoxy-3,4-dihydropyrazino[1,2-a]indol-2-yl)-3-[3-(tri-fluoromethyl)phenyl]-3,4-dihydroquinazolin-4-yl}acetate

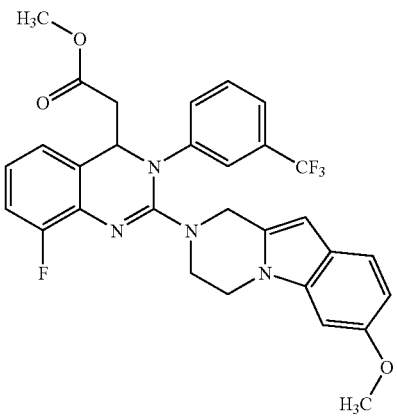 [SMILES: COC(=O)CC1c2cccc(F)c2N=C(N2CCn3c(cc4ccc(OC)cc43)C2)N1c1cccc(C(F)(F)F)c1]

Starting with 182 mg (0.4 mmol) of the iminophosphorane from Example 12A, 134 mg (0.4 mmol) of 1-isocyanato-3-(trifluoromethyl)benzene and 81 mg (0.4 mmol) of 7-methoxy-1,2,3,4-tetrahydropyrazino[1,2-a]indole from Example 35A, the general procedure [M] gives 140 mg (62% of theory) of product.

HPLC (method 1): $R_t$=4.72 min

MS (ESIpos): m/z=567 (M+H)$^+$

Example 44A

Methyl [8-fluoro-3-(2-methoxy-5-trifluoromethylphenyl)-2-(8-fluoro-3,4-dihydro-1H-pyrazino[1,2-a]indol-2-yl)-3,4-dihydroquinazolin-4-yl]acetate

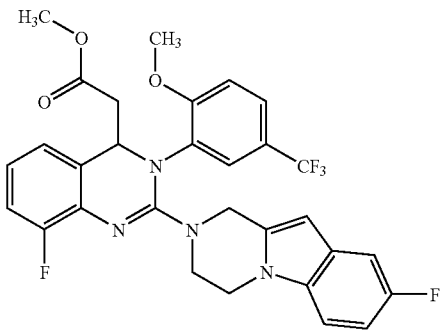 [SMILES: COC(=O)CC1c2cccc(F)c2N=C(N2CCn3c(cc4cc(F)ccc43)C2)N1c1cc(C(F)(F)F)ccc1OC]

Starting with 182 mg (0.4 mmol) of the irninophosphorane from Example 12A, 86 mg of 2-isocyanato-1-methoxy-4-(trifluoromethyl)benzene and 130 mg (0.4 mmol) of 8-fluoro-1,2,3,4-tetrahydropyrazino[1,2-a]indole from Example 36A, the general procedure [M] gives 95 mg (35% of theory) of product.

HPLC (method 1): $R_t$=4.80 min

MS (ESIpos): m/z=585 (M+H)$^+$

Example 45A

Methyl {8-fluoro-2-(8-fluoro-3,4-dihydropyrazino[1,2-a]indol-2-yl)-3-[3-(trifluoromethyl)phenyl]-3,4-dihydroquinazolin-4-yl}acetate

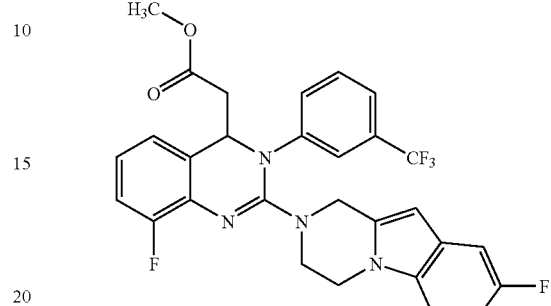

Starting with 546 mg (1.2 mmol) of the iminophosphorane from Example 12A, 402 mg (1.2 mmol) of 1-isocyanato-3-(trifluoromethyl)benzene and 240 mg (1.3 mmol) of 8-fluoro-1,2,3,4-tetrahydropyrazino[1,2-a]indole from Example 36A, the general procedure [M] gives 610 mg (86% of theory) of product.

HPLC (method 1): $R_t$=3.96 min

MS (ESIpos): m/z=555 (M+H)$^+$

Example 46A

Methyl {8-fluoro-2-(8-methyl-3,4-dihydropyrazino[1,2-a]indol-2-yl)-3-[3-(trifluoromethyl)phenyl]-3,4-dihydroquinazolin-4-yl}acetate

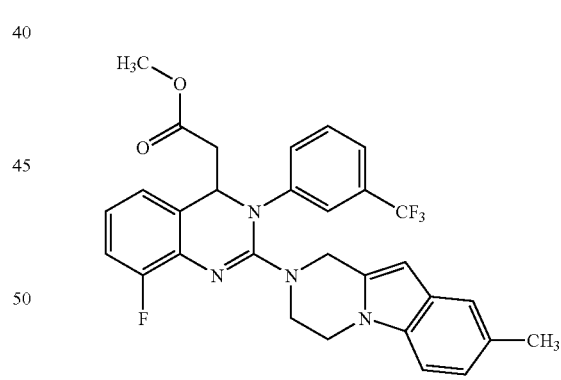

Starting with 182 mg (0.4 mmol) of the iminophosphorane from Example 12A, 134 mg (0.4 mmol) of 1-isocyanato-3-(trifluoromethyl)benzene and 80 mg (0.4 mmol) of 8-methyl-1,2,3,4-tetrahydropyrazino[1,2-a]indole from Example 37A, the general procedure [M] gives 28 mg (12% of theory) of product.

LC-MS (method 3): $R_t$=3.90 min

MS (ESIpos): m/z=551 (M+H)$^+$

General Procedure [N]: Preparation of Substituted Ethyl 2-oxo-3-(2-nitrophenyl)propanoates 16.26 mmol of potassium tert-butoxide are dissolved in 40 ml of anhydrous diethyl ether and 4 ml of absolute ethanol, 16.26 mmol of diethyl oxalate are added and the mixture is stirred at RT for 5 minutes. 14.78 mmol of the appropriate ethyl 2-oxo-3-(2-nitrophenyl)propanoate are then added, and the mixture is stirred at RT for 1 hour. Saturated ammonium chloride solution and glacial acetic acid are added to the suspension formed, and the organic phase is washed with water, saturated sodium bicarbonate solution and saturated sodium chloride solution, dried over sodium sulphate and concentrated.

Example 47A

Ethyl 2-oxo-3-(3-fluoro-2-methyl-6-nitrophenyl)propanate

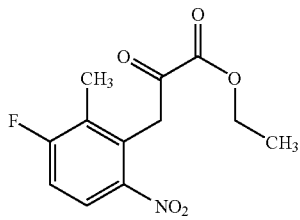

Starting with 2.50 g (14.78 mmol) of 2,3-dimethyl-4-fluoronitrobenzene, the general procedure [N] gives 2.43 g (57% of theory) of product.

HPLC (method 1): $R_f$=4.51 min

MS (DCI): m/z=287 (M+NH$_4$)$^+$

Procedure [O]: Preparation of Substituted indole-2-carboxylic esters

A mixture of 8.36 mmol of the appropriate ethyl 2-oxo-3-(2-nitrophenyl)propanoate and 75.24 mmol of iron powder in 15 ml of ethanol and 15 ml of acetic acid is heated under reflux for 2 hours. The suspension is then concentrated and the residue is suspended three times in ethyl acetate, filtered through kieselguhr and concentrated.

Example 48A

Ethyl 5-fluoro-4-methylindole-2-carboxylate

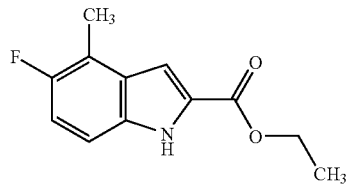 [SMILES: CCOC(=O)c1cc2c(C)c(F)ccc2[nH]1]

Starting with 2.42 g (8.36 mmol) of ethyl 2-oxo-3-(3-fluoro-2-methyl-6-nitrophenyl)propanoate, the general procedure [O] gives 1.49 g (81% of theory) of product.

HPLC (method 1): $R_f$=4.79 min

MS (DCI): m/z=222 (M+H)$^+$

Example 49A

8-Fluoro-1,2,3,4,10,10a-hexahydropyrazino[1,2-a]indole

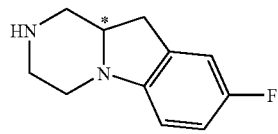

1.37 g (7.20 mmol) of the indolepiperazine from Example 36A are dissolved in 28 ml of glacial acetic acid, and 1.81 g (28.81 mmol) of sodium cyanoborohydride are added a little at a time. The mixture is stirred at RT for 16 hours, 30 ml of water are added and a little at a time, the mixture is added with stirring to 200 ml of ice-cold 10% strength aqueous sodium hydroxide solution. The aqueous phase is extracted twice with in each case 50 ml of dichloromethane. The combined organic extracts are dried over sodium sulphate and concentrated. This gives 1.07 g (77% of theory) of product.

Separation of enantiomers according to method 9 gives 510 mg of the enantiomer.

HPLC (method 1): $R_f$=3.43 min

MS (ESIpos): m/z=193 (M+H)$^+$

Example 50A

Methyl {8-fluoro-2-(8-fluoro-3,4,10,10a-tetrahydropyrazino[1,2-a]indol-2(1H)-yl)-3-[2-methoxy-5-(trifluoromethyl)phenyl]-3,4-dihydroquinazolin-4-yl}acetate

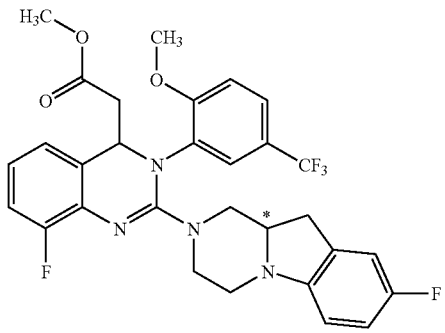 [SMILES: COC(=O)CC1c2cccc(F)c2N=C(N2CCN3c4ccc(F)cc4CC3C2)N1c1cc(C(F)(F)F)ccc1OC]

Starting with 323 mg (0.7 mmol) of the iminophosphorane from Example 12A, 154 mg of 1-isocyanato-3-(trifluoromethyl)benzene and 150 mg (0.7 mmol) of 8-fluoro-1,2,3,4,10,10a-hexahydropyrazino[1,2-a]indole from Example 49A, the general procedure [M] gives 235 mg (55% of theory) of product.

HPLC (method 1): $R_f$=4.88 min

MS (ESIpos): m/z=587 (M+H)$^+$

WORKING EXAMPLES

General Procedure [P]: Hydrolysis of the Quinazolinyl Acetic Acid Esters 1.0 equivalent of the quinazolylacetic acid ester is dissolved in dioxane, and 3.0 equivalents of 1N aqueous sodium hydroxide solution are added. The mixture is stirred at 50° C. for 16 hours, and after the reaction has ended the mixture is concentrated. The residue is then taken up in water and adjusted to pH 5 using 1N hydrochloric acid. The resulting precipitate is filtered off, washed with a little water and diethyl ether and dried at room temperature under high vacuum. If the purity of the product is not high enough, the product is purified by preparative HPLC on an RP phase (method 2).

Example 1

{8-Fluoro-2-(9-methyl-3,4-dihydropyrazino[1,2-a]indol-2(1H)-yl)-3-[3-(trifluoromethyl)phenyl]-3,4-dihydroquinazolin-4-yl}acetic acid

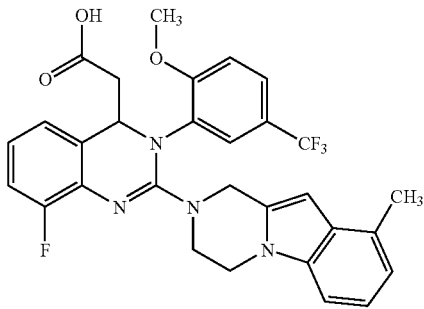 [SMILES: COc1ccc(C(F)(F)F)cc1N1C(N2CCn3c(cc4c(C)cccc43)C2)=Nc2c(F)cccc2C1CC(=O)O]

Starting with 315 mg (0.5 mmol) of the methyl ester from Example 38A, the general procedure [P] gives 330 mg (99% of theory) of product.

HPLC (method 1): $R_t$=4.75 min
MS (ESIpos): m/z=567 (M+H)$^+$
$^1$H-NMR (400 MHz, CD$_3$CN): δ [ppm]=7.51 (d, 1H); 7.16-7.02 (m, 3H); 6.97-6.78 (m, 4H); 6.25 (s, 1H); 4.89 (dd, 1H); 4.75 (dd, 1H); 4.00-3.93 (m, 1H); 3.82-3.75 (m, 2H); 3.65 (brs, 3H); 3.53-3.47 (m, 4H); 2.78 (dd, 1H); 2.40 (s, 3H).

Example 2

{8-Fluoro-2-(9-methyl-3,4-dihydropyrazino[1,2-a]indol-2(1H)-yl)-3-[3-(trifluoromethyl)phenyl]-3,4-dihydroquinazolin-4-yl}acetic acid

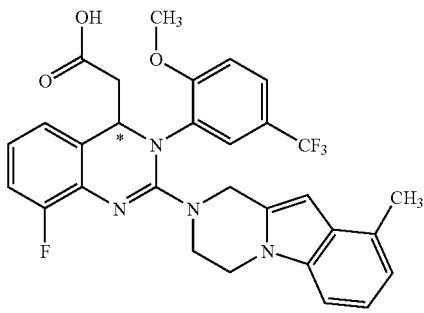 [SMILES: COc1ccc(C(F)(F)F)cc1N1C(N2CCn3c(cc4c(C)cccc43)C2)=Nc2c(F)cccc2C1CC(=O)O]

Starting with 330 mg of the quinazolinylacetic acid from Example 1, separation of enantiomers (method 4) gives 90 mg of the enantiomer.

$^1$H-NMR (400 MHz, CD$_3$CN): δ [ppm]=7.45 (d, 1H); 7.07-6.81 (m, 7H); 6.25 (s, 1H); 4.91 (dd, 1H); 4.73 (dd, 1H); 3.91-3.88 (m, 4H); 3.78-3.72 (brs, 3H); 3.54-3.48 (m, 2H); 2.87 (dd, 1H); 2.50 (dd, 1H); 2.43 (s, 3H).

Example 3

8-Fluoro-2-(9-fluoro-3,4-dihydropyrazino[1,2-a]indol-2(1H)-yl)-3-[3-(trifluoromethyl)phenyl]-3,4-dihydroquinazolin-4-yl}acetic acid

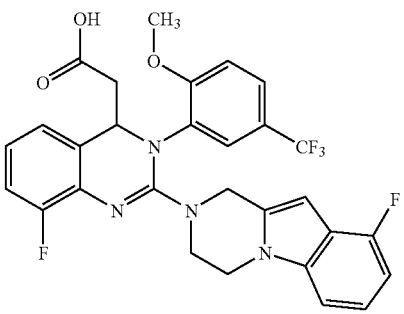 [SMILES: COc1ccc(C(F)(F)F)cc1N1C(N2CCn3c(cc4c(F)cccc43)C2)=Nc2c(F)cccc2C1CC(=O)O]

Starting with 65 mg (0.1 mmol) of the methyl ester from Example 39A, the general procedure [P] gives 62 mg (90% of theory) of product.

HPLC (method 1): $R_t$=4.68 min
MS (ESIpos): m/z=571 (M+H)$^+$
$^1$H-NMR (400 MHz, DMSO-d$_6$): δ [ppm]=7.51 (d, 1H); 7.21-6.75 (m, 7H); 6.27 (s, 1H); 4.95-4.89 (m, 1H); 4.75 (dd, 1H); 4.00 (dd, 2H); 3.82-3.78 (m, 2H); 3.69-3.63 (m, 2H); 3.56 (brs, 3H), 2.83-2.69 (m, 1H); 2.50-2.42 (m, 1H).

Example 4

8-Fluoro-2-(9-fluoro-3,4-dihydropyrazino[1,2-a]indol-2(1H)-yl)-3-[3-(trifluoromethyl)phenyl]-3,4-dihydroquinazolin-4-yl}acetic acid

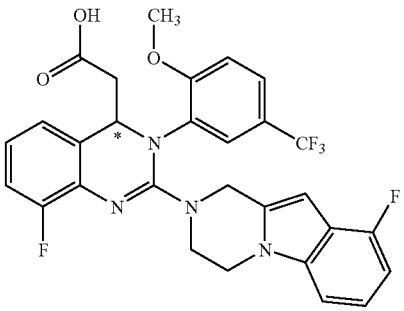 [SMILES: COc1ccc(C(F)(F)F)cc1N1C(N2CCn3c(cc4c(F)cccc43)C2)=Nc2c(F)cccc2C1CC(=O)O]

Starting with 62 mg of the quinazolinylacetic acid from Example 3, separation of enantiomers (method 4) gives 27 mg of the enantiomer.

$^1$H-NMR (400 MHz, CD$_3$CN): δ [ppm]=7.53 (d, 1H); 7.15-6.72 (m, 7H); 6.23 (s, 1H); 4.90 (dd, 1H); 4.73 (dd, 1H); 3.99-3.94 (m, 2H); 3.80-3.73 (m, 5H); 3.61-3.56 (m, 2H); 2.88 (dd, 1H); 2.52 (dd, 1H).

Example 5

{8-Fluoro-2-(9-methoxy-3,4-dihydropyrazino[1,2-a]
indol-2(1H)-yl)-3-[3-(trifluoromethyl)phenyl]-3,4-
dihydroquinazolin-4-yl}acetic acid

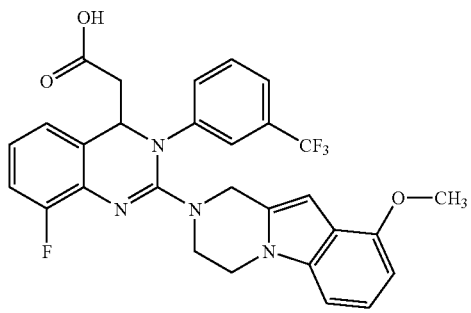 [SMILES: COc1cccc2c1cc1n2CCN(C2=Nc3c(F)cccc3C(CC(=O)O)N2c2cccc(C(F)(F)F)c2)C1]

Starting with 228 mg (0.4 mmol) of the methyl ester from Example 42A, the general procedure [P] gives 228 mg (99% of theory) of product.

HPLC (method 1): $R_t$=4.55 min

MS (ESIpos): m/z=553 (M+H)$^+$

Example 6

{8-Fluoro-2-(8-fluoro-3,4-dihydropyrazino[1,2-a]
indol-2(1H)-yl)-3-[3-(trifluoromethyl)phenyl]-3,4-
dihydroquinazolin-4-yl}acetic acid

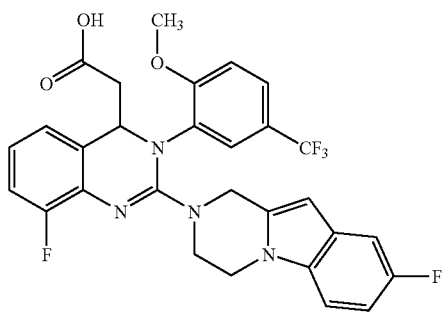 [SMILES: COc1ccc(C(F)(F)F)cc1N1C(N2CCn3c(cc4cc(F)ccc43)C2)=Nc2c(F)cccc2C1CC(=O)O]

Starting with 80 mg (0.1 mmol) of the methyl ester from Example 44A, the general procedure [P] gives 74 mg (96% of theory) of product.

HPLC (method 1): $R_t$=4.65 min

MS (ESIpos): m/z=571 (M+H)$^+$ $^1$H-NMR (400 MHz, CD$_3$CN): δ [ppm]=7.51 (d, 1H); 7.21-6.86 (m, 7H); 6.14 (s, 1H); 5.10-4.95 (m, 1H); 4.77 (dd, 1H), 4.02-3.96 (m, 4H); 3.65-3.59 (m, 5H); 3.03 (dd, 1H); 2.66 (dd, 1H).

Example 7

{8-Fluoro-2-(8-fluoro-3,4-dihydropyrazino[1,2-a]
indol-2(1H)-yl)-3-[3-(trifluoromethyl)phenyl]-3,4-
dihydroquinazolin-4-yl}acetic acid

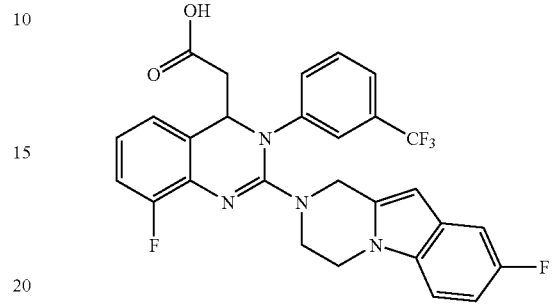

Starting with 130 mg (0.2 mmol) of the methyl ester from Example 45A, the general procedure [P] gives 120 mg (93% of theory) of product.

HPLC (method 1): $R_t$=4.63 min

MS (ESIpos): m/z=541 (M+H)$^+$

Example 8

{8-Fluoro-2-(8-fluoro-3,4-dihydropyrazino[1,2-a]
indol-2(1H)-yl)-3-[3-(trifluoromethyl)phenyl]-3,4-
dihydroquinazolin-4-yl}acetic acid

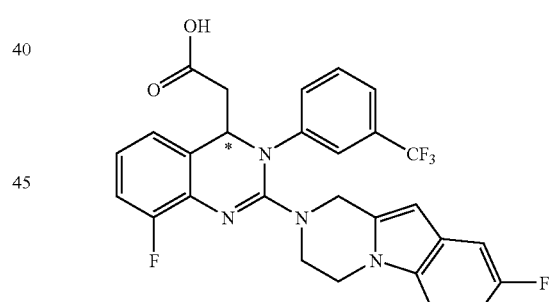

Starting with 580 mg of the quinazolinylacetic acid from Example 7, separation of enantiomers (method 4) gives 235 mg of the enantiomer.

$^1$H-NMR (400 MHz, CD$_3$CN): δ [ppm]=7.65 (s, 1H); 7.43-7.35 (m, 3H); 7.24-7.16 (m, 2H); 7.05-6.86 (m, 4H); 6.20 (s, 1H); 5.24 (dd, 1H); 4.81 (dd, 1H), 4.09-4.03 (m, 3H); 3.85-3.76 (m, 2H); 2.71 (dd, 1H); 2.52 (dd, 1H).

General Procedure [Q]: Reduction of the Dihydropyrazines to Tetrahydropyrazines 0.14 mmol of the dihydropyrazine is dissolved in 5 ml of glacial acetic acid, and 0.56 mmol of sodium cyanoborohydride is added. After one hour at room temperature (the reaction is monitored by TLC), water and ethyl acetate (10 ml each) are added to the reaction mixture. After phase separation, the aqueous phase is extracted with ethyl acetate (10 ml each), and the combined organic extracts are washed with saturated aqueous ammonium chloride solution (1 batch of 10 ml) and 0.5M hydrochloric acid (one batch of 10 ml). The extract is dried over sodium sulphate and concentrated under reduced pressure. If required, the product is purified by preparative HPLC (method 2).

Example 9

[8-Fluoro-3-[2-methoxy-5-(trifluoromethyl)phenyl]-2-(9-methyl-3,4,10,10a-tetra-hydropyrazino[1,2-a]indol-2(1H)-yl)-3,4-dihydroquinazolin-4-yl]acetic acid

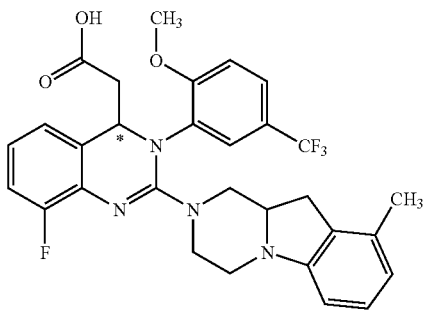 [SMILES: COc1ccc(C(F)(F)F)cc1N1C(N2CCN3c4cccc(C)c4CC3C2)=Nc2c(F)cccc2C1CC(=O)O]

Starting with 90 mg (0.16 mmol) of the enantiomer from Example 2, the general procedure [Q] gives 94 mg (99% of theory) of product.

HPLC (method 1): $R_t$=4.71 min
MS (ESIpos): m/z=569 (M+H)$^+$
$^1$H-NMR (400 MHz, CD$_3$CN): δ [ppm]=7.61 (d, 1H); 7.19-6.90 (m, 6H); 6.47 (d, 1H); 6.24 (d, 1H); 5.08 (dd, 1H); 3.92-3.82 (m, 2H); 3.76 (s, 3H); 3.43-3.37 (m, 2H); 3.23-3.16 (m, 1H); 3.09-3.01 (m, 2H); 2.97-2.89 (m, 2H); 2.48-2.40 (m, 2H); 2.14 (s, 3H).

Example 10

[8-Fluoro-3-[2-methoxy-5-(trifluoromethyl)phenyl]-2-(9-fluoro-3,4,10,10a-tetra-hydropyrazino[1,2-a]indol-2(1H)-yl)-3,4-dihydroquinazolin-4-yl]acetic acid

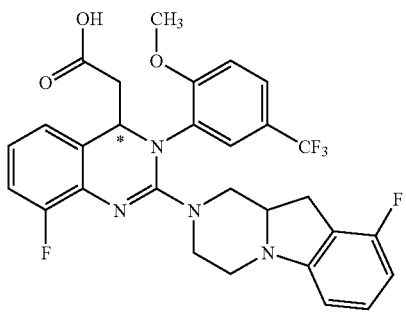 [SMILES: COc1ccc(C(F)(F)F)cc1N1C(N2CCN3c4cccc(F)c4CC3C2)=Nc2c(F)cccc2C1CC(=O)O]

Starting with 33 mg (0.06 mmol) of the enantiomer from Example 4, the general procedure [Q] gives 14 mg (39% of theory) of product.

HPLC (method 5): $R_t$=2.60 min
MS (ESIpos): m/z=573 (M+H)$^+$
$^1$H-NMR (400 MHz, CD$_3$CN): δ [ppm]=7.60 (d, 1H); 7.16-6.96 (m, 6H); 6.37 (t, 1H); 6.24 (d, 1H); 5.05 (dd, 1H); 3.98-3.88 (m, 2H); 3.77 (s, 3H); 3.50-3.40 (m, 2H); 3.16-3.10 (m, 1H); 3.04-3.00 (m, 2H); 2.73-2.66 (m, 2H); 2.53 (dd, 2H).

Example 11

[8-Fluoro-3-[3-(trifluoromethyl)phenyl]-2-(8-fluoro-3,4,10,10a-tetrahydro-pyrazino[1,2-a]indol-2(1H)-yl)-3,4-dihydroquinazolin-4-yl]acetic acid

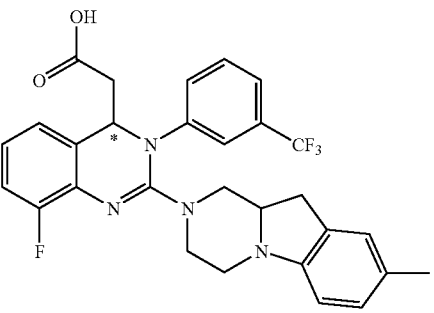 [SMILES: Cc1ccc2c(c1)CC1CN(C3=Nc4c(F)cccc4C(CC(=O)O)N3c3cccc(C(F)(F)F)c3)CCN21]

Starting with 165 mg (0.28 mmol) of the enantiomer from Example 8, the general procedure [Q] gives 155 mg (97% of theory) of product.

HPLC (method 3): $R_t$=2.66 min
MS (ESIpos): m/z=543 (M+H)$^+$
$^1$H-NMR (400 MHz, CD$_3$CN): δ [ppm]=7.77 (s, 1H); 7.60 (s, 3H); 7.23-7.20 (m, 2H); 7.08-7.06 (m, 1H); 6.83-6.77 (m, 2H); 6.36 (dd, 1H); 5.41 (dd, 1H); 3.51-3.42 (m, 2H); 3.30-2.25 (m, 1H); 3.06 (dd, 2H); 2.94 (dd, 2H); 2.74 (dd, 2H); 2.49-2.42 (m, 2H).

Example 12

{8-Fluoro-2-(8-fluoro-3,4,10,10a-tetrahydropyrazino[1,2-a]indol-2(1H)-yl)-3-[3-(trifluoromethyl)phenyl]-3,4-dihydroquinazolin-4-yl}acetic acid

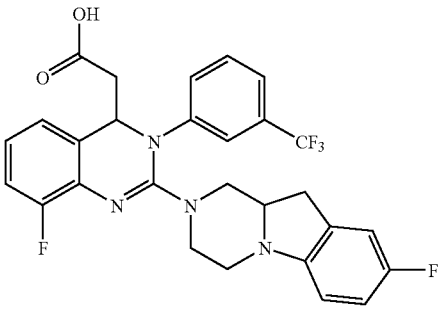 [SMILES: O=C(O)CC1c2cccc(F)c2N=C(N2CCN3c4ccc(F)cc4CC3C2)N1c1cccc(C(F)(F)F)c1]

Starting with 100 mg (0.19 mmol) of the indole derivative from Example 7, the general procedure [O] gives 40 mg (40% of theory) of product.

HPLC (method 1): R$_t$=4.62 min
MS (ESIpos): m/z=543 (M+H)$^+$
$^1$H-NMR (400 MHz, CD$_3$CN): δ [ppm]=7.79 (s, 1H); 7.69-7.56 (m, 3H); 7.32-7.26 (m, 2H); 7.13-7.08 (m, 1H); 6.88-6.76 (m, 2H); 6.40-6.38 (m, 1H); 5.42 (dd, 1H); 4.06-3.98 (m, 2H); 3.71-3.64 (m, 1H); 3.56-3.49 (m, 2H); 3.33-3.26 (m, 1H); 3.17-3.05 (m, 1H); 2.95-2.90 (m; 2H); 2.84-2.78 (m, 1H); 2.53 (dd, 1H).

Example 13

{8-Fluoro-2-(9-methoxy-2,4,10,10a-tetrahydropyrazino[1,2-a]indol-2-(1H)-yl-3-[3-(trifluoromethyl)phenyl]-3,4-dihydroquinazolin-4-yl}acetic acid

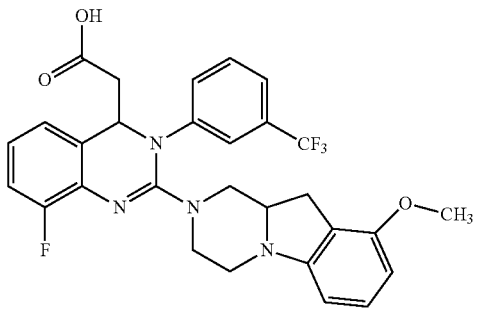 [SMILES: COc1cccc2c1CC1CN(C3=Nc4c(F)cccc4C(CC(=O)O)N3c3cccc(C(F)(F)F)c3)CCN21]

Starting with 225 mg (0.41 mmol) of the indol derivative from Example 5, the general procedure [O] gives 50 mg (22% of theory) of product.
HPLC (method 1): R$_t$=4.59 min
MS (ESIpos): m/z=555 (M+H)$^+$
$^1$H-NMR (400 MHz, CD$_3$CN): δ [ppm]=7.59 (s, 1H); 7.47-7.36 (m, 4H); 7.04-6.88 (m, 4H); 6.31 (d, 1H); 6.12 (d, 1H); 5.24 (dd, 1H); 3.74 (s, 3H); 3.50-3.34 (m, 2H); 3.05-2.98 (m, 1H); 2.90-2.71 (m, 4H); 2.60-2.51 (m, 3H).

Example 14

{8-Fluoro-2-(8-fluoro-3,4,10,10a-tetrahydropyrazino[1,2-a]indol-2(1H)-yl)-3-[2-methoxy-5-(trifluoromethyl)phenyl]-3,4-dihydroquinazolin-4-yl}acetic acid

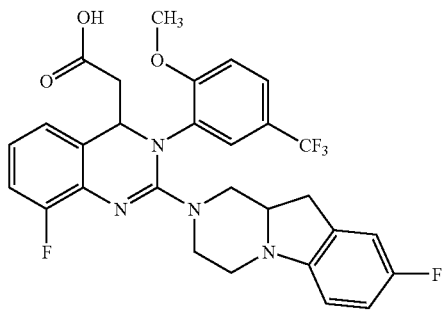 [SMILES: COc1ccc(C(F)(F)F)cc1N1C(N2CCN3c4ccc(F)cc4CC3C2)=Nc2c(F)cccc2C1CC(=O)O]

Starting with 61 mg (0.10 mmol) of the indole derivative from Example 6, the general procedure [O] gives 20 mg (36% of theory) of product.
HPLC (method 1): R$_t$=4.56 min
MS (ESIpos): m/z=573 (M+H)$^+$
$^1$H-NMR (400 MHz, CD$_3$CN): δ [ppm]=7.65 (d, 1H); 7.35-7.22 (m, 3H); 7.08-7.04 (m, 2H); 6.84 (d, 1H); 6.78-6.73 (m, 1H); 6.38-6.34 (m, 1H); 5.20 (dd, 1H); 4.05-3.80 (m, 4H); 4.57 (s, 3H); 3.40-2.77 (m, 6H); 2.97 (dd, 1H).

Example 15

{8-Fluoro-2-(8-fluoro-3,4,10,10a-tetrahydropyrazino[1,2-a]indol-2(1H)-yl)-3-[2-methoxy-5-(trifluoromethyl)phenyl]-3,4-dihydroquinazolin-4-yl]acetic acid

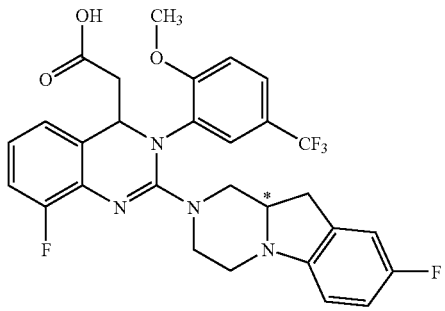 [SMILES: COc1ccc(C(F)(F)F)cc1N1C(N2CCN3c4ccc(F)cc4CC3C2)=Nc2c(F)cccc2C1CC(=O)O]

Starting with 213 mg (0.36 mmol) of the methyl ester from Example 50A, the general procedure [N] gives 207 mg (99% of theory) of product.
HPLC (method 1): R$_t$=4.68 min
MS (ESIpos): m/z=573 (M+H)$^+$
$^1$H-NMR (400 MHz, CD$_3$CN): δ [ppm]=7.48 (d, 1H); 7.33-7.29 (m, 1H); 7.14-7.05 (m, 1H); 7.02-6.98 (m, 1H); 6.90-6.82 (m, 4H); 6.36-6.30 (m, 1H); 4.89 (dd, 1H); 4.05-3.90 (m, 2H); 3.82 (s, 3H); 3.46-3.19 (m, 2H); 2.99-2.80 (m, 2H); 2.73-2.65 (m, 2H); 2.54-2.48 (m, 3H).

Example 16

{8-Fluoro-2-(8-fluoro-3,4,10,10a-tetrahydropyrazino[1,2-a]indol-2(1H)-yl)-3-[2-methoxy-5-(trifluoromethyl)phenyl]-3,4-dihydroquinazolin-4-yl}acetic acid

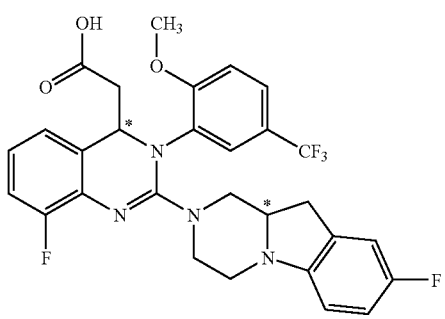 [SMILES: COc1ccc(C(F)(F)F)cc1N1C(N2CCN3c4ccc(F)cc4CC3C2)=Nc2c(F)cccc2C1CC(=O)O]

Starting with 200 mg of the quinazolinylacetic acid from Example 15, separation of enantiomers (method 4) gives 70 mg of the enantiomer.
HPLC (method 3): R$_t$=2.46 min
MS (ESIpos): m/z=573 (M+H)$^+$
$^1$H-NMR (400 MHz, CD$_3$CN): δ [ppm]=7.48 (d, 1H); 7.12-7.09 (m, 1H); 7.05-6.81 (m, 5H); 6.75-6.70 (m, 1H); 6.33-6.26 (m, 1H); 4.91 (dd, 1H); 4.05-3.89 (m, 2H); 3.82 (s, 3H); 3.29-3.19 (m, 2H); 3.03-2.97 (m, 1H); 2.91-2.82 (m, 2H); 2.77-2.70 (m, 1H); 2.56-2.44 (m, 3H).

Examples 17 to 28 from the table below can be prepared according to the general procedure [P] or [Q].

| Example | Structure | Molecular weight [g/mol] | Isomer | R$_t$ [min] | GPLC method | MS (M + H)$^+$ |
|---------|-----------|--------------------------|--------|-------------|-------------|----------------|
| 17 | 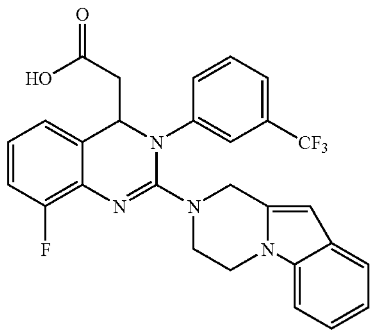 [SMILES: O=C(O)CC1c2cccc(F)c2N=C(N2CCn3c(cc4ccccc43)C2)N1c1cccc(C(F)(F)F)c1] | 522.5 | racemate | 4.63 | 1 | 523 |
| 18 | 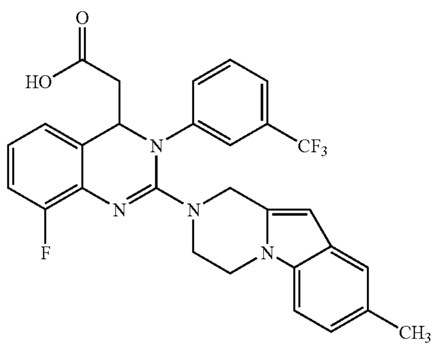 [SMILES: Cc1ccc2c(c1)cc1n2CCN(C2=Nc3c(F)cccc3C(CC(=O)O)N2c2cccc(C(F)(F)F)c2)C1] | 536.5 | racemate | 4.74 | 1 | 537 |
| 19 | 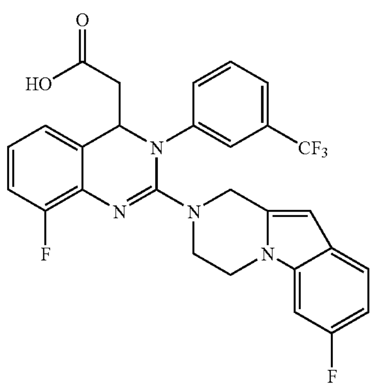 [SMILES: O=C(O)CC1c2cccc(F)c2N=C(N2CCn3c(cc4ccc(F)cc43)C2)N1c1cccc(C(F)(F)F)c1] | 540.5 | racemate | 4.59 | 1 | 541 |
| 20 | 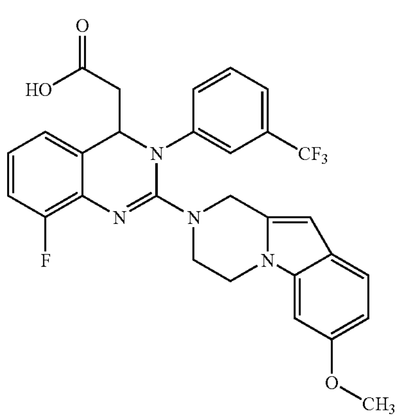 | 552.5 | racemate | 4.59 | 1 | 553 |

-continued

| Example | Structure | Molecular weight [g/mol] | Isomer | R$_t$ [min] | GPLC method | MS (M + H)$^+$ |
|---|---|---|---|---|---|---|
| 21 | 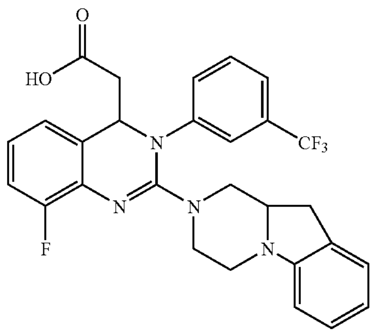 [SMILES: O=C(O)CC1c2cccc(F)c2N=C(N2CCN3c4ccccc4CC3C2)N1c1cccc(C(F)(F)F)c1] | 524.5 | diastereomer mixture | 4.56 | 1 | 525 |
| 22 | 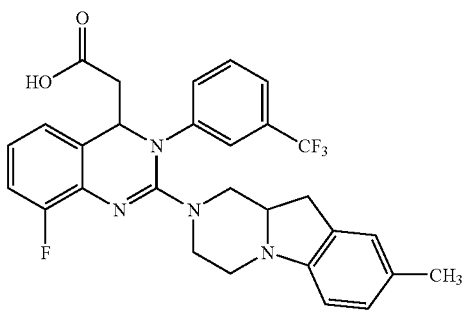 [SMILES: Cc1ccc2c(c1)CC1CN(C3=Nc4c(F)cccc4C(CC(=O)O)N3c3cccc(C(F)(F)F)c3)CCN21] | 538.5 | diastereomer mixture | 4.63 | 1 | 539 |
| 23 | 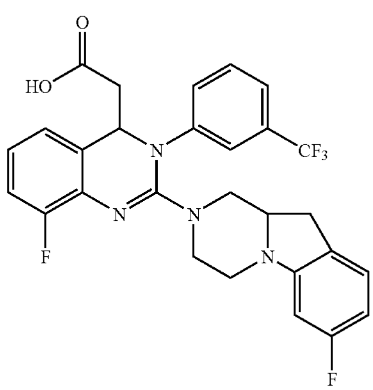 [SMILES: O=C(O)CC1c2cccc(F)c2N=C(N2CCN3c4cc(F)ccc4CC3C2)N1c1cccc(C(F)(F)F)c1] | 542.5 | isomer mixture | 4.61 | 1 | 543 |
| 24 | 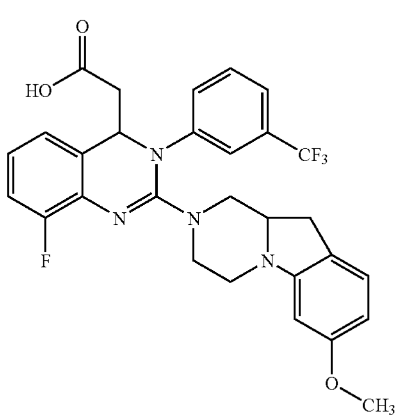 [SMILES: COc1ccc2c(c1)N1CCN(C3=Nc4c(F)cccc4C(CC(=O)O)N3c3cccc(C(F)(F)F)c3)CC1C2] | 554.5 | isomer mixture | 4.62 | 1 | 555 |

-continued

| Example | Structure | Molecular weight [g/mol] | Isomer | R$_t$ [min] | GPLC method | MS (M + H)$^+$ |
|---|---|---|---|---|---|---|
| 25 | 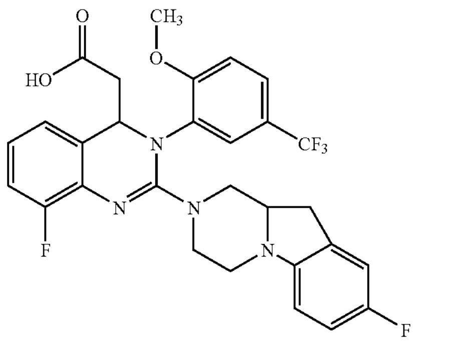 [SMILES: COc1ccc(C(F)(F)F)cc1N1C(N2CCN3c4ccc(F)cc4CC3C2)=Nc2c(F)cccc2C1CC(=O)O] | 572.5 | epimer mixture B | 4.68 | 1 | 573 |
| 26 | 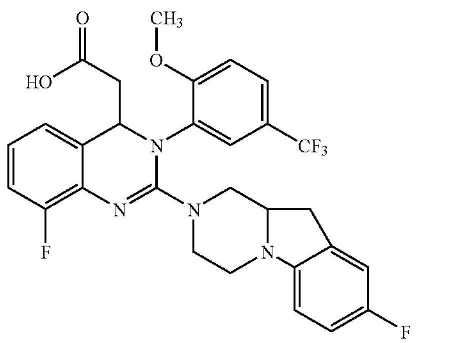 [SMILES: COc1ccc(C(F)(F)F)cc1N1C(N2CCN3c4ccc(F)cc4CC3C2)=Nc2c(F)cccc2C1CC(=O)O] | 572.5 | Diastereomer 1 | 2.48 | 3 | 573 |
| 27 | 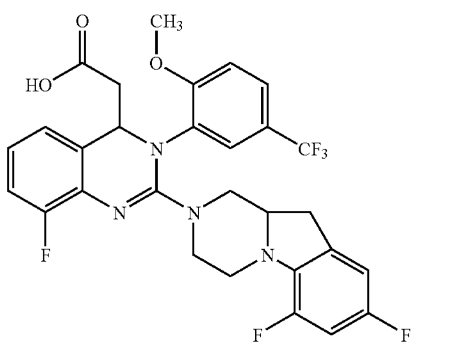 [SMILES: COc1ccc(C(F)(F)F)cc1N1C(N2CCN3c4c(F)cc(F)cc4CC3C2)=Nc2c(F)cccc2C1CC(=O)O] | 588.5 | Racemat | 4.66 | 1 | 589 |
| 28 | 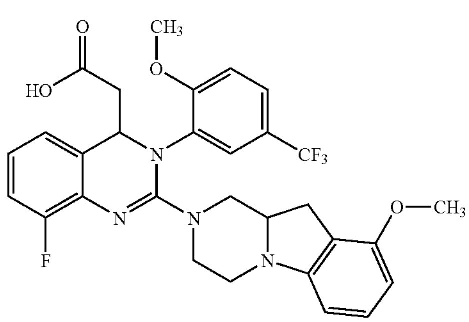 [SMILES: COc1ccc(C(F)(F)F)cc1N1C(N2CCN3c4cccc(OC)c4CC3C2)=Nc2c(F)cccc2C1CC(=O)O] | 582.56 | Racemat | 4.56 | 1 | 583 |

B. ASSESSMENT OF THE PHYSIOLOGICAL ACTIVITY

The in vitro effect of the compounds of the invention can be shown in the following assays:
Anti-HCMV (Anti-Human Cytomegalovirus) Cytopathogenicity Tests The test compounds are employed as 50 millimolar (mM) solutions in dimethyl sulphoxide (DMSO). Ganciclovir®, Foscarnet® and Cidofovir® are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. Then 150 µl portions of a suspension of 1×10$^4$ cells (human prepuce fibroblasts [NHDF]) are pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% $CO_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (Plaque Multiplier from Technomara).

The following data can be acquired from the test plates:

$CC_{50}$ (NHDF)=substance concentration in µM at which no visible cytostatic effects on the cells are evident by comparison with the untreated cell control;

$EC_{50}$ (HCMV)=substance concentration in µM which inhibits the CPE (cytopathic effect) by 50% compared with the untreated virus control;

SI (selectivity index)=$CC_{50}$ (NHDF)/$EC_{50}$ (HCMV).

Representative in vitro data for the effects of the compounds of the invention are shown in Table A:

TABLE A

| Example No. | NHDF $CC_{50}$ [µM] | HCMV $EC_{50}$ [µM] | SI HCMV |
|---|---|---|---|
| 2 | 21 | 0.09 | 233 |
| 4 | 14 | 0.12 | 117 |
| 9 | 24 | 0.04 | 600 |
| 16 | 21 | 0.02 | 1050 |

The suitability of the compounds of the invention for the treatment of HCMV infections can be shown in the following animal model:

HCMV Xenograft Gelfoam® Model
Animals:
3-4-week old female immunodeficient mice (16-18 g), Fox Chase SCID or Fox Chase SCID-NOD or SCID beige, are purchased from commercial breeders (Taconic M+B, Jackson USA). The animals are housed under sterile conditions (including bedding and feed) in isolators.

Virus Growing:
Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 10% fetal calf serum (FCS) with 10% DMSO at –40° C. After serial ten-fold dilutions of the virus-infected cells, the titre is determined on 24-well plates of confluent NHDF cells after vital staining with Neutral Red.

Preparation of the Sponges, Transplantation, Treatment and Evaluation:
Collagen sponges 1×1×1 cm in size (Gelfoam®; from Peasel & Lorey, order No. 407534; K. T. Chong et al., Abstracts of 39th Interscience Conference on Antimicrobial Agents and Chemotherapy, 1999, p. 439) are initially wetted with phosphate-buffered saline (PBS), the trapped air bubbles are removed by degassing, and then stored in MEM+10% FCS. 1×10$^6$ virus-infected NHDF cells (infection with HCMV Davis or HCMV AD169 M.O.I.=0.03) are detached 3 hours after infection and added in a drop of 20 µl of MEM, 10% of FCS, to a moist sponge. About 16 hours later, the infected sponges are incubated with 25 µl of PBS/0.1% BSA/1 mM DTT with 5 ng/µl basic fibroblast growth factor (bFGF). For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue. 6 hours after the transplantation, the mice can be treated for the first time (on the day of the operation there is one treatment). The next days, over a period of 8 days, the mice are treated with substance perorally three times a day (7.00 h and 14.00 h and 19.00 h), two times a day (8.00 h and 18.00 h) or once a day (14.00 h). The daily dose is, for example 3 or 10 or 30 or 60 or 100 mg/kg of body weight, the volume administered is 10 ml/kg of body weight. The substances are formulated in the form of a 0.5% strength Tylose suspension with 2% DMSO or a 0.5% strength Tylose suspension. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% fetal calf serum, 10% DMSO at –140° C. Evaluation takes place after serial ten-fold dilutions of the virus-infected cells by determining the titre on 24-well plates of confluent NHDF cells after vital staining with Neutral Red. The number of infected cells or infectious virus particles (infectious centre assay) after the substance treatment compared with the placebo-treated control group is determined.

CYP Inhibition Assay
To examine the mechanism-based (irreversible) inhibition of CYP3A4, different concentrations of the test substance are incubated at 37° C. with human liver microsomes (2 mg/ml microsomal protein) in potassium phosphate buffer pH 7.4 with addition of an NADPH-generating system (NADP+, glucose 6-phosphate and glucose 6-phosphate dehydrogenase). At various points of time, 2 aliquots are removed from the incubation.

The first aliquot is incubated at 37° C. 1:50 in a new incubation solution (phosphate buffer, NADPH-generating system and 10 µM midazolam) for a further 10 min. The incubation is then terminated using acetonitrile on ice, the protein is pelleted in a centrifuge at 15 000 g and the supernatant is analysed by HPLC/MS according to standard methods for formation of 1'-hydroxymidizolam.

The second aliquot is terminated with acetonitrile on ice and, using HPLC/UV/MS, analysed for remaining test substance.

Using the two sets of analytical data, parameters typical for irreversible inhibition ($k_{inact}$, $K_i$ and partition ratio r) are determined, and these parameters are used to evaluate the test substance (cf. A. Madan et al., in A. D. Rodrigues (ed.) "Drug-Drug Interaction" in "Drugs and the Pharmaceutical Science", Vol. 116, ISBN 0-8247-0283.2, Marcel Dekker Inc., New York, 2002).

C. EXEMPLARY EMBODIMENTS OF PHARMACEUTICAL COMPOSITIONS

The compounds of the invention can be converted into pharmaceutical preparations in the following ways:
Tablet:
Composition:
100 mg of the compound of Example 1, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:
Composition:

1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

Solution which can be Administered Intravenously:
Composition:

10-200 mg of the compound of Example 1, 15 g of polyethylene glycol 400 and 250 g of water for injection purposes.

Production:

The compound of Example 1 is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and trimmed caps.

The invention claimed is:

1. A compound of the formula (I)

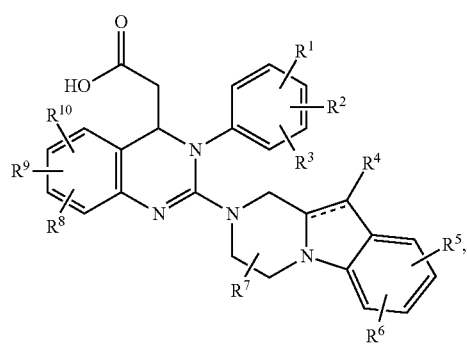

in which
╌╌╌ represents a single or double bond,
$R^1$ represents hydrogen, amino, alkyl, alkoxy, alkylamino, alkylthio, cyano, halogen, nitro or trifluoromethyl,
$R^2$ represents hydrogen, alkyl, alkoxy, alkylamino, alkylthio, cyano, halogen, nitro or trifluoromethyl,
$R^3$ represents amino, alkyl, alkoxy, alkylamino, alkylthio, cyano, halogen, nitro, trifluoromethyl, alkylsulphonyl or alkylaminosulphonyl
or
one of the radicals $R^1$, $R^2$ and $R^3$ represents hydrogen, alkyl, alkoxy, cyano, halogen, nitro or trifluoromethyl and the other two together with the carbon atoms to which they are attached form a 1,3-dioxolane, a cyclopentane ring or a cyclohexane ring,
$R^4$ represents hydrogen or alkyl,
$R^5$ represents hydrogen, alkyl, alkoxy, formyl, carboxyl, alkylcarbonyl, alkoxycarbonyl, trifluoromethyl, halogen, cyano, hydroxyl, amino, alkylamino, aminocarbonyl or nitro,
where alkyl may be substituted by 1 to 3 substituents, where the substituents are selected independently of one another from the group consisting of halogen, amino, alkylamino, hydroxyl and aryl,
$R^6$ represents hydrogen, alkyl, alkoxy, formyl, carboxyl, alkylcarbonyl, alkoxycarbonyl, trifluoromethyl, halogen, cyano, hydroxyl, amino, alkylamino, aminocarbonyl or nitro,
where alkyl may be substituted by 1 to 3 substituents, where the substituents are selected independently of one another from the group consisting of halogen, amino, alkylamino, hydroxyl and aryl
or
$R^5$ and $R^6$ together with the carbon atoms to which they are attached form a 1,3-dioxolane, a cyclopentane ring or a cyclohexane ring,
$R^7$ represents hydrogen or alkyl,
$R^8$ represents hydrogen, alkyl, alkoxy, alkylamino, alkylthio, formyl, carboxyl, aminocarbonyl, alkylaminocarbonyl, alkylcarbonyl, alkoxycarbonyl, trifluoromethyl, halogen, cyano, hydroxyl, nitro or a 5- to 7-membered heterocycle which is attached via nitrogen,
$R^9$ represents hydrogen, alkyl, alkoxy, alkylthio, formyl, carboxyl, alkylcarbonyl, alkoxycarbonyl, trifluoromethyl, halogen, cyano, hydroxyl or nitro,
$R^{10}$ represents hydrogen, alkyl, alkoxy, alkylthio, formyl, carboxyl, alkylcarbonyl, alkoxycarbonyl, trifluoromethyl, halogen, cyano, hydroxyl or nitro,
or a salt thereof.

2. The compound according to claim 1, wherein:
╌╌╌ represents a single or double bond,
$R^1$ represents hydrogen, $C_1$-$C_6$-alkyl, $C_1$-$C_6$-alkoxy, $C_1$-$C_6$-alkylthio, fluorine or chlorine,
$R^2$ represents hydrogen, $C_1$-$C_6$-alkyl, $C_1$-$C_6$-alkoxy, $C_1$-$C_6$-alkylthio, fluorine or chlorine,
$R^3$ represents $C_1$-$C_4$-alkyl, cyano, fluorine, chlorine, nitro or trifluoromethyl,
or
one of the radicals $R^1$, $R^2$ and $R^3$ represents hydrogen, $C_1$-$C_3$-alkyl, $C_1$-$C_3$-alkoxy, cyano, halogen, nitro or trifluoromethyl and the other two together with the carbon atoms to which they are attached form a cyclopentane ring or a cyclohexane ring,
$R^4$ represents hydrogen,
$R^5$ represents hydrogen, $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino or nitro,
$R^6$ represents hydrogen, $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino or nitro
or
$R^5$ and $R^6$ together with the carbon atoms to which they are attached form a 1,3-dioxolane,
$R^7$ represents hydrogen or methyl,
$R^8$ represents $C_1$-$C_3$-alkyl, $C_1$-$C_3$-alkoxy, carboxyl, aminocarbonyl, $C_1$-$C_3$-alkylaminocarbonyl, trifluoromethyl, fluorine, chlorine, cyano, hydroxyl or nitro, $R^9$ represents hydrogen, $C_1$-$C_3$-alkyl, $C_1$-$C_3$-alkoxy, fluorine, chlorine, cyano or hydroxyl and $R^{10}$ represents hydrogen, $C_1$-$C_3$-alkyl, $C_1$-$C_3$-alkoxy, fluorine, chlorine, cyano or hydroxyl.

3. The compound according to claim 1 or 2, wherein:

┄┄┄┄ represents a single or double bond, $R^1$ represents hydrogen, methyl, methoxy, methylthio, fluorine or chlorine, $R^2$ represents hydrogen, $R^3$ represents methyl, cyano, fluorine, chlorine, nitro or trifluoromethyl, $R^4$ represents hydrogen, $R^5$ represents hydrogen, methyl, methoxy, fluorine or chlorine, $R^6$ represents hydrogen, methyl, methoxy, fluorine or chlorine, $R^7$ represents hydrogen, $R^8$ represents aminocarbonyl, fluorine, chlorine, cyano or hydroxyl, $R^9$ represents hydrogen and $R^{10}$ represents hydrogen.

4. The compound according to claim 1, wherein ┄┄┄┄ represents a single bond.

5. The compound according to claim 1, wherein $R^1$ represents hydrogen, methyl, methoxy or fluorine.

6. The compound according to claim 1, wherein $R^1$ represents methoxy.

7. The compound according to claim 1, wherein $R^1$ is attached to the phenyl ring via the position ortho to the point of attachment of the phenyl ring.

8. The compound according to claim 1, wherein $R^2$ represents hydrogen.

9. The compound according to claim 1, wherein $R^3$ represents trifluoromethyl, chlorine, methyl, isopropyl or tert-butyl.

10. The compound according to claim 1, wherein $R^3$ represents trifluoromethyl, chlorine or methyl.

11. The compound according to claim 1, wherein $R^1$ is attached to the phenyl ring via the position ortho to the point of attachment of the phenyl ring and $R^3$ is attached to the phenyl ring via the position meta to the point of attachment of the phenyl ring, which position is opposite to that of $R^1$.

12. The compound according to claim 1, wherein $R^4$ represents hydrogen.

13. The compound according to claim 1, wherein $R^5$ represents hydrogen, methyl, methoxy, fluorine or chlorine.

14. The compound according to claim 1, wherein $R^6$ represents hydrogen, methyl, methoxy or fluorine.

15. The compound according to claim 1, wherein $R^7$ represents hydrogen.

16. The compound according to claim 1, wherein $R^8$ represents fluorine.

17. The compound according to claim 1, wherein $R^9$ represents hydrogen.

18. The compound according to claim 1, wherein $R^{10}$ represents hydrogen, methyl or fluorine.

19. A process for preparing a compound of the formula (I) according to claim 1, wherein:

according to process [P], a compound of the formula

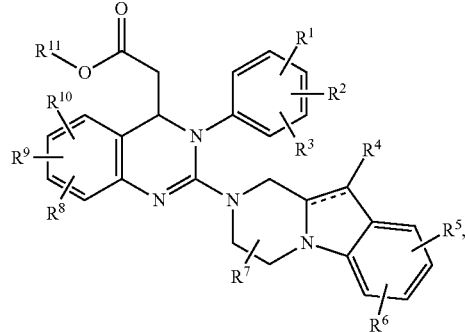

(II)

in which

┄┄┄┄ $R^1$, $R^2$, $R^3$, $R^4$, $R^5$, $R^6$, $R^7$, $R^8$, $R^9$ and $R^{10}$ are as defined in claim 1, and $R^{11}$ represents alkyl, is reacted with a base, or, according to process [Q], a compound of the formula

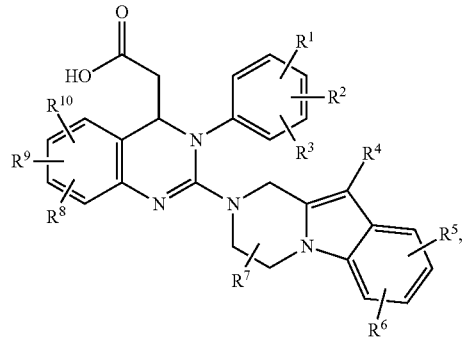

(Ib)

in which $R^1$, $R^2$, $R^3$, $R^4$, $R^5$, $R^6$, $R^7$, $R^8$, $R^9$ and $R^{10}$ are as defined in claim 1 is, by reaction with reducing agent, converted into a compound of the formula

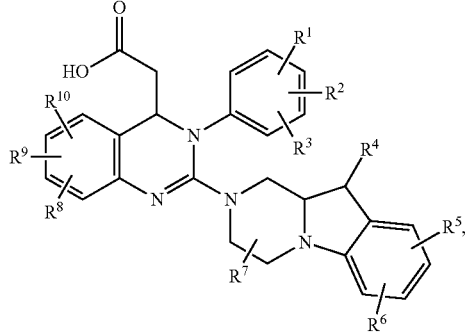

(Ic)

in which
R$^1$, R$^2$, R$^3$, R$^4$, R$^5$, R$^6$, R$^7$, R$^8$, R$^9$ and R$^{10}$ are as defined in claim 1.

20. A medicament comprising a compound according to claim 1 or a salt thereof in combination with an inert nontoxic pharmaceutically acceptable auxiliary.

21. A method for preparing a medicament comprising bringing a compound according to claim 1 or a salt thereof into a pharmaceutically acceptable administration form.

22. A method for-treating a viral infection in a human, or the prophylaxis, or treatment and prophylaxis of a viral infection in an immuno-compromised human, comprising administering an antivirally effective amount of at least one compound according to claim 1 or a salt thereof to a human in need thereof, wherein the viral infection is an infection with the human cytomegalovirus (HCMV) or another representative of the group Herpes viridae.

23. The process of claim 19, wherein in subprocess [P], R$^{11}$ represents methyl or ethyl.

* * * * *